US012594282B2

(12) United States Patent
Lu et al.

(10) Patent No.: US 12,594,282 B2
(45) Date of Patent: Apr. 7, 2026

(54) USE OF SMALL MOLECULE COMPOUNDS IN THE TREATMENT OF DISEASES MEDIATED BY LUNG EPITHELIAL CELL INJURY AND/OR VASCULAR ENDOTHELIAL CELL INJURY

(71) Applicant: Guangzhou Cellprotek Pharmaceutical Co., Ltd., Guangdong (CN)

(72) Inventors: Bingzheng Lu, Guangdong (CN); Yupin Chen, Guangdong (CN); Yana Wang, Guangdong (CN); Jiayu Huang, Guangdong (CN); Chunhui Huang, Guangdong (CN); Jiesi Chen, Guangdong (CN)

(73) Assignee: Guangzhou Cellprotek Pharmaceutical Co., Ltd., Guangdong (CN)

( * ) Notice: Subject to any disclaimer, the term of this patent is extended or adjusted under 35 U.S.C. 154(b) by 882 days.

(21) Appl. No.: 17/802,870

(22) PCT Filed: Feb. 26, 2021

(86) PCT No.: PCT/CN2021/078061
§ 371 (c)(1),
(2) Date: Aug. 26, 2022

(87) PCT Pub. No.: WO2021/170073
PCT Pub. Date: Sep. 2, 2021

(65) Prior Publication Data

US 2023/0089123 A1 Mar. 23, 2023

(30) Foreign Application Priority Data

Feb. 28, 2020 (CN) ......................... 202010128617.7
Sep. 30, 2020 (CN) ......................... 202011069298.3

(51) Int. Cl.
*A61K 31/568* (2006.01)
*A61P 11/00* (2006.01)

(52) U.S. Cl.
CPC ............ *A61K 31/568* (2013.01); *A61P 11/00* (2018.01)

(58) Field of Classification Search
CPC ................................ A61P 11/00; A61K 31/56
See application file for complete search history.

(56) References Cited

U.S. PATENT DOCUMENTS 10,835,539 B2 11/2020 Yin et al.
2017/0042909 A1* 2/2017 Yin .......................... A61P 9/12

FOREIGN PATENT DOCUMENTS

| | | | |
|---|---|---|---|
| CN | 101472579 | A | 7/2009 |
| CN | 104853758 | A | 8/2015 |
| CN | 108125965 | A | 6/2018 |
| CN | 109985046 | A | 7/2019 |
| CN | 109985049 | A | 7/2019 |
| EP | 3733190 | A1 | 11/2020 |
| WO | WO2004019953 | A1 | 3/2004 |
| WO | WO2006002907 | A1 | 1/2006 |
| WO | WO2007064691 | A1 | 6/2007 |
| WO | WO2008039566 | A2 | 4/2008 |
| WO | WO2014085474 | A1 | 6/2014 |
| WO | WO2019129179 | A1 | 7/2019 |

OTHER PUBLICATIONS

Lu et al., "SMARCB1 Promotes Ubiquitination and Degradation of NR4A3 via Direct Interaction Driven by ROS in Vascular Endothelial Cell Injury," Oxid. Med. Cell Longev. Oct. 23, 2020;2020:2048210. PMID: 33163142. (Year: 2020).*
Min Yan, et al. "Neuroprotectant androst-3β, 5α, 6β-triol suppresses TNF-a-induced endothelial adhesion molecules expression and neutrophil adhesion to endothelial cells by attenuation of CYLD-NF-KB pathway," *Biochemical and Biophysical Research Communications* 483 (2017) 892-896, Elsevier.
International Search Report and Written Opinion in International Application PCT/CN2021/078061 mailed May 27, 2021.
Wang et al., "Ablation of endothelial PFKFb3 protects mice from acute lung injury in LPS-induced endotoxemia," Pharmacological Research 146: 104292, 15 pages (Aug. 2019).
Zhou et al., "Synthetic steroid of 5α-Androst-3ß,5α,6ß-Triol alleviates acute lung injury via inhibiting inflammation and oxidative stress," International Immunopharmacology 129:111486, 11 pages (Mar. 10, 2024).

* cited by examiner

*Primary Examiner* — Theodore R. Howell
(74) *Attorney, Agent, or Firm* — FOLEY & LARDNER LLP

(57) ABSTRACT

Disclosed is use of 5α-androst-3β,5,6β-triol or an analogue, a deuterated compound or a pharmaceutically acceptable salt thereof in the manufacture of a medicament for the treatment of a pulmonary disease in a patient. These compounds can significantly inhibit the up-regulation of PFKFB3 expression, significantly inhibit the accumulation of lactate, significantly reduce vascular endothelial cell injury, significantly reduce alveolar epithelial cell injury, significantly inhibit alveolar septum thickening, significantly reduce alveolar damage, and thus can be used to treat diseases mediated by lung epithelial cell injury and/or vascular endothelial cell injury, such as in the lung.

11 Claims, 8 Drawing Sheets

USE OF SMALL MOLECULE COMPOUNDS IN THE TREATMENT OF DISEASES MEDIATED BY LUNG EPITHELIAL CELL INJURY AND/OR VASCULAR ENDOTHELIAL CELL INJURY

CROSS-REFERENCE TO RELATED APPLICATIONS

This application is a U.S. National Phase Application under 35 U.S.C. § 371 of International Patent Application No. PCT/CN2021/078061, filed on Feb. 26, 2021, which in turns claims priority to Chinese Application No. 202010128617.7, filed Feb. 28, 2020 and Chinese Application No. 202011069298.3, filed Sep. 30, 2020, the content of each application is hereby incorporated by reference in its entirety.

TECHNICAL FIELD

The present invention relates to use of small molecule compounds in the treatment of diseases mediated by lung epithelial cell injury and/or vascular endothelial cell injury, in particular to the above use of 5α-androst-3β,5,6β-triol (sometimes referred to herein as "YC-6" or "YC6") and its analogues, especially to the use of these compounds in the treatment of lung injury and cerebral small vessel disease.

BACKGROUND

Lung injury is common in lung diseases, especially diseases such as acute lung injury/acute respiratory distress syndrome (ALI/ARDS), pulmonary arterial hypertension, sepsis and other diseases. These diseases seriously endanger health, and some of them are related to high mortality.

Acute lung injury (ALI) refers to acute hypoxic respiratory insufficiency or failure caused by various serious non-cardiac internal and external pulmonary pathogenic factors (such as viral infection, bacterial infection, trauma, shock, ischemia-reperfusion, acute pancreatitis, inhalation injury, diffuse alveolar damage, poisoning caused by other toxins, etc.), with pathological features manifesting as pulmonary edema, alveolar collapse and dilatation, alveolar wall thickening and inflammatory cell infiltration due to increased alveolar epithelial and pulmonary capillary endothelial permeability (Butt et al., 2016). The severe stage of ALI is called acute respiratory distress syndrome (ARDS), which is characterized by refractory hypoxemia and respiratory distress, and may lead to respiratory failure, multiple organ dysfunction and even death. The mortality rate of ALI/ARDS can reach 40% to 60%, and there is still no effective drug therapy.

29% of Corona Virus Disease 2019 (COVID-19) cases caused by SARS-CoV-2 (Wu F et al, 2020) are complicated by acute respiratory distress syndrome (ARDS) (Huang C et al, 2020). COVID-19 inducing ARDS has been further confirmed by pathological evidence (Xu Z et al, 2020). Bilateral diffuse alveolar damage with cellular fibromyxoid exudate, pulmonary edema, shedding of lung cells, and hyaline membrane formation was found in the histological examination of two deceased patients, which severely affected the ventilation/gas-exchange function of the lungs, and developed into ARDS. How to prevent patients from becoming severe and treat tens of thousands of severe/critical patients are urgent medical and social needs.

The alveoli are the basic units for gas exchange in the lungs, and their inner surfaces are covered with type I and type II alveolar epithelial cells. Type I flat cells make up 90% of the alveolar surface area and are prone to injury. Type II stereocells constitute the remaining 10% of the alveolar surface area and are not susceptible to damage, and their functions include surfactant production, ion transport, and proliferation and differentiation following injury to type I cells. In addition to forming a dense barrier to sequester exogenous pathogens, the alveolar epithelium also maintains lung homeostasis and relative sterility by interacting with immune cells through its surface receptors and secretory products. Among them, alveolar epithelial cells play a dominant role in lung homeostasis and are directly related to lung-related diseases such as acute lung injury, pulmonary fibrosis, and tissue remodeling diseases.

Pulmonary vascular endothelial cells form the monolayer lining the vasculature. Due to their physiological location being exposed to various injury factors, such as LPS, endotoxin, TNF-α and oxidative stress, pulmonary vascular endothelial cells are target cells attacked by various lung injury factors and play an important role in the pathogenesis of ALI/ARDS. Studies have shown that bronchoalveolar lavage fluid from patients at risk or with early and advanced ARDS is cytotoxic to human pulmonary microvascular endothelial cells. For pulmonary vascular endothelial cells, the action of bacterial endotoxin (lippopolysaccharide, LPS), cytokines, oxygen free radicals, etc., leads to increased capillary permeability and increased pulmonary water content, resulting in pulmonary edema and dyspnea; secretion and release of various inflammatory mediators and cytokines make the pro-inflammatory and anti-inflammatory mediators unbalanced, and the coagulation and anticoagulation systems are unbalanced, causing pulmonary microcirculation disorders and pulmonary arterial hypertension, which can promote pulmonary interstitial edema, pulmonary hemorrhage and progressive dyspnea, leading to progressive hypoxemia and respiratory distress in the patient (Du Jingxia et al., 2012). Screening of drugs that can alleviate the damage of pulmonary vascular endothelial cells caused by unfavorable factors is expected to be useful in the prevention and treatment of various lung injury-related diseases, including various infectious pneumonia, acute lung injury, ARDS, pulmonary arterial hypertension, etc.

Phosphofructokinase-2/fructose-2,6-bisphosphatase 3 (PFKFB3) is a key regulatory protein in the glycolysis pathway in the sugar metabolism pathway. PFKFB3 plays a key role in lung injury. Inhibitors of the glycolytic enzyme PFKFB3 can improve survival, lung inflammation, increased lactate, and apoptotic damage in lung cells in cecal ligation and puncture (CLP)-induced ALI mice (Gong Y et al, 2017). Anaerobic glycolysis is also an important factor in sepsis-related ALI cell apoptosis, and PFKFB3 inhibitor can significantly reduce lung injury in LPS-induced acute lung injury/acute respiratory distress syndrome (ALI/ARDS) experimental animals (Wang L et al. al, 2019). After the specific knockout of PFKFB3 in vascular endothelial cells, the glycolysis level of endothelial cells was significantly reduced, and the expression of growth factors, pro-inflammatory cytokines and cell adhesion factors was reduced, which in turn inhibited the abnormal proliferation of pulmonary vascular smooth muscle cells, and the infiltration of inflammatory cells around pulmonary vessels, inhibiting the development of hypoxia-induced pulmonary arterial hypertension (Cao Y, 2019). After the specific knockout of Pfkfb3 in smooth muscle cells, the glycolytic metabolite lactate was reduced, resulting in decreased ERK1/2-dependent phosphorylation of calpain-2, leading to decreased collagen synthesis in pulmonary vascular smooth muscle cells, and the abnormal proliferation of smooth muscle cells was also weakened, thereby inhibiting pulmonary vascular remodeling during the development of pulmonary arterial hypertension (Kovacs et al., 2019).

The blood-brain barrier (BBB) is the cell interface between the central nervous system and the circulatory system, and is a type of brain barrier. The structure of the blood-brain barrier includes vascular endothelial cells, pericytes, astrocyte foot processes, basement membrane, etc., which together with neurons constitutes a neurovascular unit. Vascular endothelial cells constitute the anatomical basis of the blood-brain barrier, allowing various selective transport systems to transport nutrients and other substances into and out of the brain, ensuring low permeability of the intercellular space to hydrophilic solutes. More and more evidence from clinical studies, neuropathology, epidemiology and animal models has shown that the destruction of the blood-brain barrier caused by increased vascular permeability is one of the initiating factors of cerebral small vessel disease. Vascular endothelial cell injury and endothelial tissue dysfunction can lead to increased permeability of the blood-brain barrier, leading to blood components entering the potential perivascular space and brain parenchyma, causing damage to nerve cells and glial cells. It has been reported that the increased permeability of the blood-brain barrier predates the appearance of neurological damage and clinical symptoms.

A number of clinical studies have shown that patients with cerebral small vessel disease have reduced cerebral blood flow and impaired vascular autoregulation. PET and MRI examinations have shown that patients with white matter hyperintensity present a state of hypoperfusion, increased vascular permeability and damage to the blood-brain barrier, while there is no significant change in gray matter, suggesting that the damaged area of the blood-brain barrier is dominated by white matter. Studies have shown that patients with white matter lesions have long-term changes in the permeability of the blood-brain barrier. At the same time, the development of white matter hyperintensity adjacent to the cortex is related to the degree of damage to the blood-brain barrier. Changes in the permeability of the blood-brain barrier cause plasma extravasation and surrounding tissue damage, which is an important reason for the continuous deterioration of white matter lesions. Studies using DCE-MRI have shown that there is a potential leakage of the blood-brain barrier in more brain tissue in patients with cerebral small vessel disease, further supporting that the impaired integrity of the blood-brain barrier is the main pathogenesis of cerebral small vessel disease.

At present, there is still a lack of effective drugs to treat lung injury in various pulmonary diseases or vascular endothelial cell injury-mediated diseases. Therefore, it is of great clinical significance to provide a drug that can effectively treat these diseases.

SUMMARY

The inventor unexpectedly found that the compound 5α-androst-4,5,6β-triol can significantly inhibit the up-regulation of PFKFB3 expression, significantly inhibit the accumulation of lactate, reduce vascular endothelial cell injury, reduce alveolar epithelial cell injury, inhibit alveolar septum thickening, reduce alveolar damage and pulmonary inflammatory cell infiltration, and thus can be used to treat various diseases mediated by alveolar epithelial cell injury and/or vascular endothelial cell injury.

Accordingly, in one aspect, the present invention provides use of a compound of formula I:

(formula I)

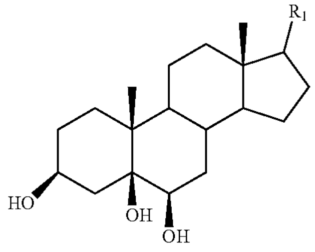

or a deuterated compound or a pharmaceutically acceptable salt thereof in the manufacture of a medicament for preventing or treating a disease mediated by lung epithelial cell injury and/or vascular endothelial cell injury, wherein $R_1$ is selected from H, —CN, fluoro, chloro, $C_{1-10}$ alkyl, fluoro or chloro substituted $C_{1-10}$ alkyl, $C_{1-10}$ alkoxy, fluoro or chloro substituted $C_{1-10}$ alkoxy, and $C_{3-10}$ cycloalkyl. In some embodiments, $R_1$ is H, $—CHCH_2CH_3$, $—CH(CH_3)_2$, $—CH(CH_2)_3CH_3$, or $—CH(CH_3)(CH_2)_3CH(CH_3)_2$. In a preferred embodiment, $R_1$ is H.

In another aspect, the present invention provides any one of the above compounds, a deuterated compound or a pharmaceutically acceptable salt thereof for use in the prevention or treatment of a disease mediated by lung epithelial cell injury and/or vascular endothelial cell injury.

In yet another aspect, the present invention provides a method of preventing or treating a disease mediated by lung epithelial cell injury and/or vascular endothelial cell injury, the method comprising administering to a subject in need thereof a prophylactically or therapeutically effective amount of any one of the above compounds, a deuterated compound or a pharmaceutically acceptable salt thereof.

In the present disclosure, for any one of the above aspects: In some embodiments, the disease mediated by lung epithelial cell injury and/or vascular endothelial cell injury is one or more of acute lung injury, acute respiratory distress syndrome, pulmonary arterial hypertension, pulmonary edema, pulmonary fibrosis, chronic lung disease in premature infants, chronic obstructive pulmonary disease, pneumocystis disease, and pulmonary embolism. In some embodiments, the acute lung injury, acute respiratory distress syndrome, pulmonary arterial hypertension, or pulmonary edema is caused by hyperoxia, viral infection, bacterial infection, trauma, shock, ischemia-reperfusion, acute pancreatitis, inhalation injury, diffuse alveolar damage, and/or poisoning. In some embodiments, the acute lung injury, acute respiratory distress syndrome, pulmonary arterial hypertension, or pulmonary edema is caused by hyperoxia, viral infection, bacterial infection, trauma, shock, ischemia-reperfusion, acute pancreatitis, inhalation injury, diffuse alveolar damage, and/or poisoning, and is not caused by hypoxia (for example, high altitude hypoxia). In some embodiments, the virus is a coronavirus (for example, SARS-CoV-2), influenza virus, respiratory syncytial virus, adenovirus, parainfluenza virus, measles virus, cytomegalovirus, or a combination thereof. In some embodiments, the virus is a coronavirus (for example, SARS-CoV-2). In some embodiments, the acute lung injury is a lung injury caused by a surgery, and the surgery is, for example, pneumonectomy such as sublobectomy, lobectomy or total pneumonectomy, lung tumor resection or lung transplantation. In some embodiments, the pulmonary fibrosis is idiopathic pulmonary fibrosis or pneumoconiosis.

In the present disclosure, for any one of the above aspects: In some embodiments, the disease mediated by vascular endothelial cell injury comprises cerebral small vessel disease mediated by blood-brain barrier disruption, but does not comprise cerebral microbleed, cerebral stroke and cerebral edema. In some embodiments, the blood-brain barrier disruption is manifested as increased permeability of blood-brain barrier. In some embodiments, the blood-brain barrier disruption is manifested as injury of vascular endothelial cells of blood-brain barrier. In some embodiments, the cerebral small vessel disease mediated by blood-brain barrier disruption involves clinical manifestation of cognitive impairment, gait disturbance, mood disturbance, urinary incontinence and/or depression. In some embodiments, the cerebral small vessel disease mediated by blood-brain barrier disruption involves imaging manifestation comprising white matter lesion. In some embodiments, the cerebral small vessel disease mediated by blood-brain barrier disruption involves imaging manifestation of only white matter lesion.

In the present disclosure, for any one of the above aspects: In some embodiments, the disease mediated by lung epithelial cell injury and/or vascular endothelial cell injury is cardiovascular disease or diabetic vascular complication. In some embodiments, the cardiovascular disease is selected from one or more of acute myocardial infarction (AMI), angina pectoris, coronary heart disease, ischemic heart disease, heart failure, hypertension, and cardiovascular interventional thrombosis. In some embodiments, the diabetic vascular complication is one or more of diabetic retinopathy, diabetic nephropathy, and diabetic impaired wound healing.

DETAILED DESCRIPTION OF THE INVENTION

Figure 1:
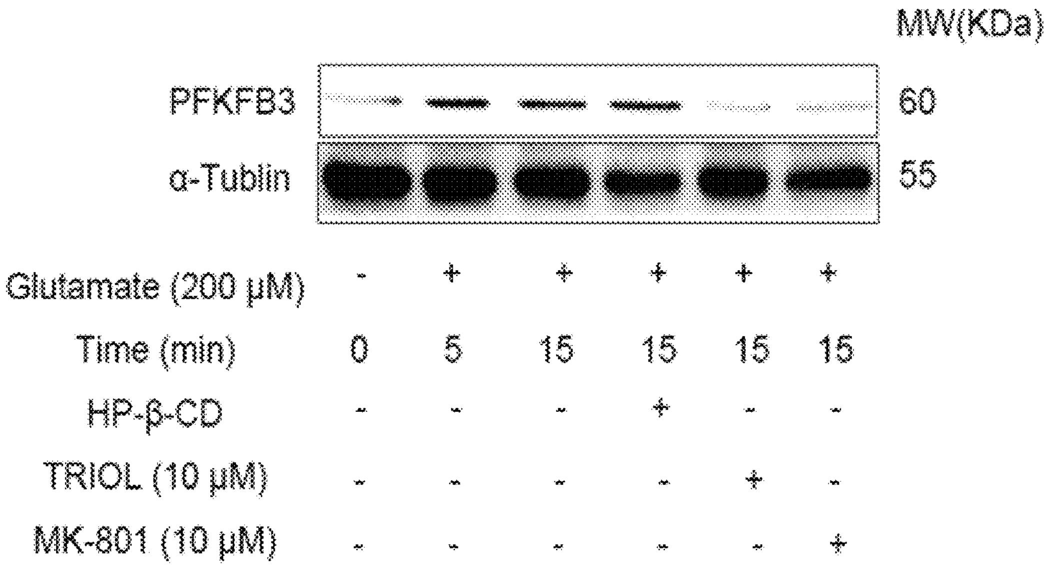
FIG. 1. YC-6 significantly inhibited glutamate-induced increase in PFKFB3 expression. Cultured primary neurons were stimulated with 200 μM glutamate for 5 mins and 15 mins. Pre-incubating with 10 μM YC-6, the corresponding solvent HP-β-CD, and 10 μM NMDA receptor blocker MK-801 for 20 mins was performed in the experiment group, solvent control group and positive drug control group. PFKFB3 immunoblot analysis was performed after protein collection.

As used herein, the term "composition" refers to a formulation suitable for administration to an intended animal subject for therapeutic purposes, which comprises at least one pharmaceutically active component, such as a compound. Optionally, the composition further comprises at least one pharmaceutically acceptable carrier or excipient.

The term "pharmaceutically acceptable" means that the substance does not have the property that, considering the disease or condition to be treated and the respective route of administration, will allow rational and prudent medical practitioners to avoid administering the substance to the patient. For example, for injectables, it is often required that such substance is substantially sterile.

As used herein, the terms "prophylactically effective amount" and "therapeutically effective amount" mean that the substance and the amount of the substance are effective to prevent, alleviate or ameliorate one or more symptoms of a disease or condition, and/or prolong the survival of the subject receiving the treatment.

As used herein, "treatment" includes the administration of a compound of the present application or a pharmaceutically acceptable salt thereof to alleviate the symptoms or complications of a disease or condition, or to eliminate the disease or condition. The term "alleviate" as used herein is used to describe the process of reducing the severity of signs or symptoms of a disorder. Symptoms can be alleviated but not eliminated. In one embodiment, administration of the pharmaceutical composition of the present application results in the elimination of signs or symptoms.

As used herein, "prevention" or "preventing" includes administration of a compound of the present application, or a pharmaceutically acceptable salt thereof, to prevent or stop the development of a particular disease, symptom, or complication.

As used herein, the term "$C_{1-10}$" or "$C_{3-10}$" or similar expressions means having 1 to 10 or 3 to 10 carbon atoms. For example, $C_{1-10}$ to alkyl refers to an alkyl group having 1 to 10 carbon atoms, such as methyl, ethyl, propyl, isopropyl, butyl, isobutyl, pentyl, decyl, and the like.

The term "disease mediated by lung epithelial cell injury and/or vascular endothelial cell injury" as used herein includes diseases mediated by lung epithelial cell injury, diseases mediated by vascular endothelial cell injury, and diseases mediated by lung epithelial cell injury and vascular endothelial cell injury.

Compound of Formula I, or a Deuterated Compound or a Pharmaceutically Acceptable Salt Thereof Compounds that are applicable in the methods or uses of the present invention include the compound of formula I:

(formula I)

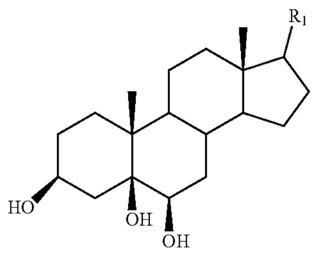

or a deuterated compound or a pharmaceutically acceptable salt thereof, wherein $R_1$ is selected from H, —CN, fluoro, chloro, $C_{1-10}$ alkyl, fluoro or chloro substituted $C_{1-10}$ alkyl, $C_{1-10}$ alkoxy, fluoro or chloro substituted $C_{1-10}$ alkoxy, and $C_{3-10}$ cycloalkyl. The compound of formula I, or a deuterated compound or a pharmaceutically acceptable salt thereof, is also referred to herein as "compound(s) of the invention/application" or "the compounds)".

In one embodiment, $R_1$ is H, and the compound is 5α-androst-3β,5,6β-triol (abbreviated as "YC-6" or "YC6"), which has the structure of formula (II):

(formula II)

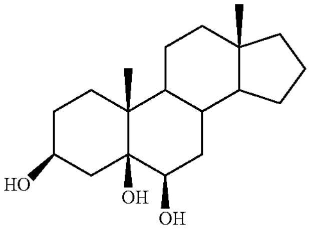

In one embodiment, $R_1$ is —$CHCH_2CH_3$, and the compound is 17-propylene-androst-3β,5α,6β-triol. In one embodiment, is —$CH(CH_3)_2$, and the compound is 17-isopropyl-androst-3β,5α,6β-triol. In one embodiment, $R_1$ is —$CH(CH_2)_3CH_3$, and the compound is 17-butyl-androst-3β,5α,6β-triol. In one embodiment, $R_1$ is —$CH(CH_3)(CH_2)_3CH(CH_3)_2$, and the compound is cholestane-3β, 5α, 6β-triol.

The compounds of the present invention can be formulated in the form of pharmaceutically acceptable salts. The expected pharmaceutically acceptable salt forms include, but are not limited to, mono-, di-, tri-, and tetra-salts. Pharmaceutically acceptable salts are non-toxic at the amount and concentration to which they are administered. The preparation of such salts can facilitate pharmacological uses by changing the physical properties of the compound without preventing it from exerting physiological effects. Useful changes in physical properties include lowering the melting point to facilitate transmucosal administration, and increasing solubility to facilitate administration of higher concentrations of drugs.

Pharmaceutically acceptable salts include acid addition salts, such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate salts. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid and quinic acid.

When acidic functional groups such as carboxylic acids or phenols are present, pharmaceutically acceptable salts also include base addition salts, such as those containing benzathine penicillin, chloroprocaine, choline, diethanolamine, ethanolamine, tert-butylamine, ethylenediamine, meglumine, procaine, aluminum, calcium, lithium, magnesium, potassium, sodium, ammonium, alkylamine and zinc. Such salts can be prepared using appropriate corresponding bases.

Pharmaceutically acceptable salts can be prepared through standard techniques. For example, the compound in its free base form can be dissolved in a suitable solvent, such as an aqueous solution or a water-alcohol solution containing a suitable acid, and then the solution is evaporated for separation. In another example, the salt is prepared by reacting the free base with an acid in an organic solvent.

Thus, for example, if the specific compound is a base, the desired pharmaceutically acceptable salt can be prepared by any suitable method available in the art, for example, by treating the free base with an inorganic acid such as hydrochloric acid, hydrobromic acid, sulfuric acid, nitric acid, phosphoric, or the like, or an organic acid such as acetic acid, maleic acid, succinic acid, mandelic acid, fumaric acid, malonic acid, pyruvic acid, oxalic acid, glycolic acid, salicylic acid, pyranosidyl acid such as glucuronic acid or galacturonic acid, α-hydroxy acid such as citric acid or tartaric acid, amino acid such as aspartic acid or glutamic acid, aromatic acid such as benzoic acid or cinnamic acid, sulfonic acid such as p-toluenesulfonic acid or ethanesulfonic acid or the like.

Similarly, if the specific compound is an acid, the desired pharmaceutically acceptable salt can be prepared by any suitable method, for example, by treating the free acid with an inorganic base or an organic base, such as an amine (primary, secondary or tertiary amine), alkali metal hydroxides or alkaline earth metal hydroxides or the like. Illustrative examples of suitable salts include organic salts derived from amino acids (such as L-glycine, L-lysine, and L-arginine), ammonia, primary, secondary, and tertiary amines, and cyclic amines (such as hydroxyethylpyrrolidine, piperidine, morpholine and piperazine), and inorganic salts derived from sodium, calcium, potassium, magnesium, manganese, iron, copper, zinc, aluminum and lithium.

The pharmaceutically acceptable salts of the compounds can exist as complexes. Examples of complexes include 8-chlorotheophylline complexes (such as, for example, diphenhydramate:diphenhydramine 8-chlorotheophylline (1:1) complex; Dramamine) and various complexes comprising cyclodextrin.

The present invention is also intended to include the use of pharmaceutically acceptable deuterated compounds or other non-radioactive substituted compounds. Deuteration is to replace one or more or all of the hydrogen in the active molecular group of the drug with isotope deuterium. Because it is non-toxic and non-radioactive, and it is about 6-9 times more stable than the carbon-hydrogen bond, it can close the metabolic site and prolong the half-life of the drug, thereby reducing the therapeutic dose without affecting the pharmacological activity of the drug, thus it is considered to be an excellent modification method.

Pharmaceutical Composition

Another aspect of the present invention provides a pharmaceutical composition comprising an effective amount of a compound of formula I, or a deuterated compound or a pharmaceutically acceptable salt thereof, and a pharmaceutically acceptable carrier.

In the present invention, "pharmaceutical composition" refers to a composition comprising a compound of formula I and a pharmaceutically acceptable carrier, wherein the compound and the pharmaceutically acceptable carrier are present in the composition in a mixed form. The composition will generally be used in the treatment of human subjects. However, they can also be used to treat similar or same conditions in other animal subjects. In this context, the terms "subject", "animal subject" and similar terms refer to human and non-human vertebrates, such as mammals, such as non-human primates, competitive animals and commercial animals, such as horses, cattle, pigs, sheep, rodents, and pets (such as dogs and cats).

The appropriate dosage form depends in part on the use or route of administration, for example, it can be oral, transdermal, transmucosal, by inhalation or by injection (parenteral). Such dosage forms should enable the compound to reach target cells. Other factors are well known in the art and include considerations such as toxicity and dosage forms that delay the compound or composition from exerting its effects.

Carriers or excipients can be used to produce the composition. The carriers or excipients can be selected to facilitate administration of the compound. Examples of carriers include calcium carbonate, calcium phosphate, various sugars (such as lactose, glucose, or sucrose), or starch types, cellulose derivatives, gelatin, vegetable oils, polyethylene glycol, and physiologically compatible solvents. Examples of physiologically compatible solvents include sterile water for injection (WFI) solutions, saline solutions, and glucose.

The composition or components of the composition can be administered by different routes, including intravenous, intraperitoneal, subcutaneous, intramuscular, oral, transmucosal, rectal, transdermal, or inhalation routes. In some embodiments, injections or lyophilized powder injections are preferred. For oral administration, for example, the compound may be formulated into conventional oral dosage forms such as capsules and tablets, and liquid preparations such as syrups, elixirs and concentrated drops.

Pharmaceutical preparations for oral use can be obtained, for example, by combining the composition or its components with solid excipients, optionally grinding the resulting mixture, and treating the mixture of particles after adding suitable adjuvants (if necessary), thereby obtaining tablets or dragees. Suitable excipients are, in particular, fillers such as sugars including lactose, sucrose, mannitol or sorbitol; cellulose preparations such as corn starch, wheat starch, rice starch, potato starch, gelatin, tragacanth, methyl cellulose, hydroxypropyl methyl cellulose, sodium carboxymethyl cellulose (CMC) and/or polyvinylpyrrolidone (PVP: povidone). If desired, disintegrating agents may be added, such as cross-linked polyvinylpyrrolidone, agar, or alginic acid or their salts, such as sodium alginate.

Alternatively, injections (parenteral administration) can be used, for example intramuscular, intravenous, intraperitoneal and/or subcutaneous injection. For injection, the composition of the invention or its components are formulated as a sterile liquid solution, preferably in a physiologically compatible buffer or solution, such as saline solution, Hank's solution or Ringer's solution. In addition, the composition or its components can be formulated in a solid form and re-dissolved or suspended immediately before use. It can also be produced in the form of lyophilized powder.

Administration can also be by transmucosal, topical or transdermal means. For transmucosal, topical or transdermal administration, penetrants suitable for the barrier to be penetrated are used in the formulation. Such penetrants are generally known in the art and include, for example, for transmucosal administration, bile salts and fusidic acid derivatives. In addition, detergents can be used to promote penetration. Transmucosal administration, for example, can be by nasal spray or suppository (via rectum or vagina).

The effective amount of various components to be administered can be determined by standard procedures, taking into account factors such as $IC_{50}$ of the compound, the biological half-life of the compound, the age, size, and body weight of the subject, and the conditions associated with the subject. The importance of these and other factors is well known to those of ordinary skill in the art. Generally, the dosage will be between about 0.01 mg/kg and 50 mg/kg of the subject to be treated, preferably between 0.1 mg/kg and 20 mg/kg. Multiple doses can be used.

The composition of the present invention or its components can also be used in combination with other therapeutic agents for treating the same disease. Such combined use includes administration of these compounds and one or more other therapeutic agents at different times, or simultaneous use of these compounds and one or more other therapeutic agents. In some embodiments, the dosage of one or more compounds of the invention or other therapeutic agents used in combination can be modified, for example, by methods known to those of skill in the art to reduce the dose relative to the compound or therapeutic agent used alone.

It is to be understood that the combined use or combination includes use with other therapies, drugs, medical procedures, etc., wherein the other therapies or procedures may be administered at a time different from the composition of the present invention or its components (eg, in a short period of time (such as a few hours, such as 1, 2, 3, 4-24 hours) or in a longer period of time (such as 1-2 days, 2-4 days, 4-7 days, 1-4 weeks)) or at the same time as the composition of the invention or its components. The combined use also includes use with one-time or infrequently administered therapies or medical procedures (such as a surgery), accompanied by administration of the composition of the invention or its components within a short period of time or a longer period of time before or after the other therapies or procedures. In some embodiments, the present invention is used to deliver the composition of the present invention or its components and one or more other pharmaceutical therapeutic agents, and they are delivered by same or different routes.

The combined administration of any route of administration includes the delivery of the composition of the invention or its components and one or more other pharmaceutical therapeutic agents in any formulation by the same route of administration, including formulations in which the two compounds are chemically linked and retain their respective therapeutic activity when administered. In one aspect, the other drug therapy can be co-administered with the composition of the invention or its components. The combined use by co-administration includes the administration of the co-formulation or chemically linked compounds, or the administration in a short period of time (eg, within one hour, within 2 hours, within 3 hours, up to within 24 hours) of two or more compounds in independent formulations, which are administered by the same or different routes.

Co-administration of independent formulations includes co-administration by delivery via one device, such as the same inhalation device, the same syringe, etc., or administration by different devices within a short period of time relative to each other. A co-formulation of a compound of the present invention and one or more additional pharmacotherapies delivered by the same route of administration includes preparing the materials together so that they can be administered by one device, including combining different compounds in one formulation, or modifying compounds so that they are chemically linked together but still retain their biological activity. Such chemically linked compounds may include a linker that separates the two active ingredients, where the linker is substantially maintained in the body, or may be degraded in the body.

Medical Use and Method of Treatment

In one aspect, the present invention provides use of any one of the compounds, a deuterated compound or a pharmaceutically acceptable salt thereof in the manufacture of a medicament for preventing or treating a disease mediated by lung epithelial cell injury and/or vascular endothelial cell injury. In some embodiments, the disease mediated by lung epithelial cell injury and/or vascular endothelial cell injury is selected from one or more of acute lung injury, acute respiratory distress syndrome, pulmonary arterial hypertension, pulmonary edema, pulmonary fibrosis, chronic lung disease in premature infants, chronic obstructive pulmonary disease, pneumocystis disease, and pulmonary embolism. In some embodiments, the acute lung injury, acute respiratory distress syndrome, pulmonary arterial hypertension, or pulmonary edema is caused by hyperoxia, viral infection, bacterial infection, trauma, shock, ischemia-reperfusion, acute pancreatitis, inhalation injury, diffuse alveolar damage, and/or poisoning. In some embodiments, the acute lung injury, acute respiratory distress syndrome, pulmonary arterial hypertension, or pulmonary edema is caused by hyperoxia, viral infection, bacterial infection, trauma, shock, ischemia-reperfusion, acute pancreatitis, inhalation injury, diffuse alveolar damage, and/or poisoning, and is not caused by hypoxia. In some embodiments, the virus is a coronavirus (for example, SARS-CoV-2), influenza virus, respiratory syncytial virus, adenovirus, parainfluenza virus, measles virus, cytomegalovirus, or a combination thereof. In some embodiments, the virus is a coronavirus (for example, SARS-CoV-2). In some embodiments, the acute lung injury is a lung injury caused by a surgery, and the surgery is, for example, pneumonectomy such as sublobectomy, lobectomy or total pneumonectomy, lung tumor resection or lung transplantation. In some embodiments, the pulmonary fibrosis is idiopathic pulmonary fibrosis or pneumoconiosis. In a preferred embodiment, the disease mediated by lung epithelial cell injury and/or vascular endothelial cell injury is lung injury. In a preferred embodiment, the disease mediated by lung epithelial cell injury and/or vascular endothelial cell injury is acute lung injury. In a preferred embodiment, the disease mediated by lung epithelial cell injury and/or vascular endothelial cell injury is acute respiratory distress syndrome. In a preferred embodiment, the disease mediated by lung epithelial cell injury and/or vascular endothelial cell injury is pulmonary arterial hypertension.

In some embodiments, the disease mediated by vascular endothelial cell injury comprises cerebral small vessel disease mediated by blood-brain barrier disruption (or damage), but does not comprise cerebral microbleed, cerebral stroke and cerebral edema. In some embodiments, the blood-brain barrier disruption is manifested as increased permeability of blood-brain barrier. In some embodiments, the blood-brain barrier disruption is manifested as injury of vascular endothelial cells of blood-brain barrier. In some embodiments, the cerebral small vessel disease mediated by blood-brain barrier disruption involves clinical manifestation of cognitive impairment, gait disturbance, mood disturbance, urinary incontinence and/or depression. In some embodiments, the cerebral small vessel disease mediated by blood-brain barrier disruption involves imaging manifestation comprising white matter lesion. In some embodiments, the cerebral small vessel disease mediated by blood-brain barrier disruption involves imaging manifestation of only white matter lesion.

In some embodiments, the disease mediated by lung epithelial cell injury and/or vascular endothelial cell injury is cardiovascular disease or diabetic vascular complication. In some embodiments, the cardiovascular disease is selected from one or more of acute myocardial infarction (AMI), angina pectoris, coronary heart disease, ischemic heart disease, heart failure, hypertension, and cardiovascular interventional thrombosis. In some embodiments, the diabetic vascular complication is one or more of diabetic retinopathy, diabetic nephropathy, and diabetic impaired wound healing.

In one aspect, the present invention provides a method of preventing or treating a disease mediated by lung epithelial cell injury and/or vascular endothelial cell injury, the method comprising administering to a subject in need thereof a prophylactically or therapeutically effective amount of any one of the compounds of the present invention, a deuterated compound or a pharmaceutically acceptable salt thereof. In some embodiments, the disease mediated by lung epithelial cell injury and/or vascular endothelial cell injury is selected from one or more of acute lung injury, acute respiratory distress syndrome, pulmonary arterial hypertension, pulmonary edema, pulmonary fibrosis, chronic lung disease in premature infants, chronic obstructive pulmonary disease, pneumocystis disease, and pulmonary embolism. In some embodiments, the acute lung injury, acute respiratory distress syndrome, pulmonary arterial hypertension, or pulmonary edema is caused by hyperoxia, viral infection, bacterial infection, trauma, shock, ischemia-reperfusion, acute pancreatitis, inhalation injury, diffuse alveolar damage, and/or poisoning. In some embodiments, the acute lung injury, acute respiratory distress syndrome, pulmonary arterial hypertension, or pulmonary edema is caused by hyperoxia, viral infection, bacterial infection, trauma, shock, ischemia-reperfusion, acute pancreatitis, inhalation injury, diffuse alveolar damage, and/or poisoning, and is not caused by hypoxia. In some embodiments, the virus is a coronavirus (for example, SARS-CoV-2), influenza virus, respiratory syncytial virus, adenovirus, parainfluenza virus, measles virus, cytomegalovirus, or a combination thereof. In some embodiments, the virus is a coronavirus (for example, SARS-CoV-2). In some embodiments, the acute lung injury is a lung injury caused by a surgery, and the surgery is, for example, pneumonectomy such as sublobectomy, lobectomy or total pneumonectomy, lung tumor resection or lung transplantation. In some embodiments, the pulmonary fibrosis is idiopathic pulmonary fibrosis or pneumoconiosis. In a preferred embodiment, the disease mediated by lung epithelial cell injury and/or vascular endothelial cell injury is lung injury. In a preferred embodiment, the disease mediated by lung epithelial cell injury and/or vascular endothelial cell injury is acute lung injury. In a preferred embodiment, the disease mediated by lung epithelial cell injury and/or vascular endothelial cell injury is acute respiratory distress syndrome. In a preferred embodiment, the disease mediated by lung epithelial cell injury and/or vascular endothelial cell injury is pulmonary arterial hypertension.

In some embodiments, the disease mediated by vascular endothelial cell injury comprises cerebral small vessel disease mediated by blood-brain barrier disruption (or damage), but does not comprise cerebral microbleed, cerebral stroke and cerebral edema. In some embodiments, the blood-brain barrier disruption is manifested as increased permeability of blood-brain barrier. In some embodiments, the blood-brain barrier disruption is manifested as injury of vascular endothelial cells of blood-brain barrier. In some embodiments, the cerebral small vessel disease mediated by blood-brain barrier disruption involves clinical manifestation of cognitive impairment, gait disturbance, mood disturbance, urinary incontinence and/or depression. In some embodiments, the cerebral small vessel disease mediated by blood-brain barrier disruption involves imaging manifestation comprising white matter lesion. In some embodiments, the cerebral small vessel disease mediated by blood-brain barrier disruption involves imaging manifestation of only white matter lesion.

In some embodiments, the disease mediated by lung epithelial cell injury and/or vascular endothelial cell injury is cardiovascular disease or diabetic vascular complication. In some embodiments, the cardiovascular disease is selected from one or more of acute myocardial infarction (AMI), angina pectoris, coronary heart disease, ischemic heart disease, heart failure, hypertension, and cardiovascular interventional thrombosis. In some embodiments, the diabetic vascular complication is one or more of diabetic retinopathy, diabetic nephropathy, and diabetic impaired wound healing.

In another aspect, the present invention provides any one of the compounds of the present invention, a deuterated compound or a pharmaceutically acceptable salt thereof for use in the prevention or treatment of a disease mediated by lung epithelial cell injury and/or vascular endothelial cell injury. In some embodiments, the disease mediated by lung epithelial cell injury and/or vascular endothelial cell injury is selected from one or more of acute lung injury, acute respiratory distress syndrome, pulmonary arterial hypertension, pulmonary edema, pulmonary fibrosis, chronic lung disease in premature infants, chronic obstructive pulmonary disease, pneumocystis disease, and pulmonary embolism. In some embodiments, the acute lung injury, acute respiratory distress syndrome, pulmonary arterial hypertension, or pulmonary edema is caused by hyperoxia, viral infection, bacterial infection, trauma, shock, ischemia-reperfusion, acute pancreatitis, inhalation injury, diffuse alveolar damage, and/or poisoning. In some embodiments, the acute lung injury, acute respiratory distress syndrome, pulmonary arterial hypertension, or pulmonary edema is caused by hyperoxia, viral infection, bacterial infection, trauma, shock, ischemia-reperfusion, acute pancreatitis, inhalation injury, diffuse alveolar damage, and/or poisoning, and is not caused by hypoxia. In some embodiments, the virus is a coronavirus (for example, SARS-CoV-2), influenza virus, respiratory syncytial virus, adenovirus, parainfluenza virus, measles virus, cytomegalovirus, or a combination thereof. In some embodiments, the virus is a coronavirus (for example, SARS-CoV-2). In some embodiments, the acute lung injury is a lung injury caused by a surgery, and the surgery is, for example, pneumonectomy such as sublobectomy, lobectomy or total pneumonectomy, lung tumor resection or lung transplantation. In some embodiments, the pulmonary fibrosis is idiopathic pulmonary fibrosis or pneumoconiosis. In a preferred embodiment, the disease mediated by lung epithelial cell injury and/or vascular endothelial cell injury is lung injury. In a preferred embodiment, the disease mediated by lung epithelial cell injury and/or vascular endothelial cell injury is acute lung injury. In a preferred embodiment, the disease mediated by lung epithelial cell injury and/or vascular endothelial cell injury is acute respiratory distress syndrome. In a preferred embodiment, the disease mediated by lung epithelial cell injury and/or vascular endothelial cell injury is pulmonary arterial hypertension.

In some embodiments, the disease mediated by vascular endothelial cell injury comprises cerebral small vessel disease mediated by blood-brain barrier disruption (or damage), but does not comprise cerebral microbleed, cerebral stroke and cerebral edema. In some embodiments, the blood-brain barrier disruption is manifested as increased permeability of blood-brain barrier. In some embodiments, the blood-brain barrier disruption is manifested as injury of vascular endothelial cells of blood-brain barrier. In some embodiments, the cerebral small vessel disease mediated by blood-brain barrier disruption involves clinical manifestation of cognitive impairment, gait disturbance, mood disturbance, urinary incontinence and/or depression. In some embodiments, the cerebral small vessel disease mediated by blood-brain barrier disruption involves imaging manifestation comprising white matter lesion. In some embodiments, the cerebral small vessel disease mediated by blood-brain barrier disruption involves imaging manifestation of only white matter lesion.

In some embodiments, the disease mediated by lung epithelial cell injury and/or vascular endothelial cell injury is cardiovascular disease or diabetic vascular complication. In some embodiments, the cardiovascular disease is selected from one or more of acute myocardial infarction (AMI), angina pectoris, coronary heart disease, ischemic heart disease, heart failure, hypertension, and cardiovascular interventional thrombosis. In some embodiments, the diabetic vascular complication is one or more of diabetic retinopathy, diabetic nephropathy, and diabetic impaired wound healing.

Disease or Condition

Acute Lung Injury/Acute Respiratory Distress Syndrome (ALI/ARDS)

Acute lung injury (ALI) is acute, progressive hypoxic respiratory failure characterized by lung inflammation and increased pulmonary microvascular permeability, the final stage of which is acute respiratory distress syndrome (ARDS). A variety of factors can cause acute lung injury, including, but not limited to, hyperoxia, viral infection, bacterial infection, trauma, shock, ischemia-reperfusion, acute pancreatitis, inhalation injury, diffuse alveolar damage, poisoning, and the like, for example, acute lung injury/acute respiratory distress syndrome in or caused by infectious pneumonia (eg, bacterial pneumonia or viral pneumonia). For example, the pathophysiological features of Corona Virus Disease 2019 (COVID-19) include: SARS-CoV-2 mainly attacks the lungs of the patient, resulting in diffuse alveolar damage, accompanied by cellular fibromyxoid exudates, shedding of lung cells and formation of hyaline membranes in the patient, which seriously affects the ventilation/air-exchange function of the lungs and develops into acute respiratory distress syndrome. Clinical studies have also found that in some patients, after the viral nucleic acid test turns negative, lung damage still exists for a long time, and even worsens.

In ALI, the changes of pulmonary vascular endothelial cells are particularly striking, and the damage of vascular endothelial cells has been regarded as the pathological basis of the occurrence and development of ALI. Pulmonary arterial hypertension (PAH) is one of the main manifestations of early ALI caused by various reasons. PAH can promote pulmonary interstitial edema, pulmonary hemorrhage, and progressive dyspnea, and the dysfunction and damage of pulmonary vascular endothelial cells may be a key factor in the formation of PAH during ALI. Vascular endothelial dysfunction occurs before vascular changes and is reversible. Therefore, it is of great significance to study and understand its occurrence and development and its regulatory mechanism for the prevention and treatment of ALI.

Studies have confirmed that the destruction of alveolar epithelial cells in deceased patients with ALI/ARDS is very obvious. Although pulmonary capillaries are also damaged to a certain extent, the damage to epithelial cells is still the main one. At the liquid-air interface of the alveoli, alveolar epithelial cells maintain the alveolar lining fluid with the proper water and solute content, which is essential for gas exchange and host resistance to pathogens such as viruses and bacteria. If the endothelial permeability in the lung changes, the edema fluid in the pulmonary interstitium and alveolar space will eventually be cleared, and pulmonary fibrosis will not develop. Conversely, massive damage to alveolar epithelial cells increases protein permeability, reduces alveolar fluid and alveolar protein clearance, and then leads to accumulation of large molecular weight proteins and disordered repair in alveoli, leading to deterioration of gas exchange. The destruction of the alveolar epithelium during ALI results in the shedding of epithelial cells and the consequent infiltration of protein-rich edema fluid into the alveolar space, accelerating the destruction of the alveolar barrier. Forms of epithelial cell destruction include apoptosis and necrosis. These two types of death can be found in the alveolar wall in ARDS deceased patients and in animal models of hyperoxia, LPS stimulation, cecal ligation and perforation, ischemia-reperfusion, ventilator-associated pneumonia and ventilator-associated lung injury. Necrosis leads to membrane disruption and cytoplasmic spillage, which further stimulates the inflammatory response. Necrosis can be directly caused by mechanical damage to the alveoli, hyperthermia, ischemia, or stimulation of bacterial products. Apoptosis is associated with surface death receptors and causes only mild inflammation through cellular clearance. Extensive epithelial cell apoptosis and dissociation leads to exposure of the cell basement membrane to inflammatory products in the alveolar space, such as oxidants, proteases, and inflammatory factors. Epithelial cell destruction leading to fibroblast proliferation and collagen formation may lead to pulmonary fibrosis. Following injury, restoration of alveolar epithelial integrity is important for restoring normal epithelial cell function and clearing pulmonary edema. A series of studies have confirmed that certain factors produced by ALI/ARDS patients themselves or whether they enter the alveolar space can promote epithelial repair. These soluble factors come from fibroblasts, macrophages, endothelial cells, epithelial cells, extracellular matrix, plasma exudates, constitutive cytokines, chemokines, growth factors, prostaglandins, and mechanistic components in the patient's lungs. Although there are many studies on ALI/ARDS, the patient mortality rate remains high. Due to the poor efficacy of existing drug therapy, the treatment of ARDS is still based on supportive care. One of the major factors determining the severity and progression of ALI is the degree of alveolar epithelial injury. From the perspective of the treatment of epithelial cells, inhibiting the early damage of epithelial cells, accelerating the repair of epithelial cells, and eliminating pulmonary edema will be effective measures to improve the survival of patients.

Idiopathic Pulmonary Fibrosis (IPF)

Idiopathic pulmonary fibrosis (IPF) is a lung disease caused by damage to alveolar epithelial cells and abnormal tissue proliferation. Studies have confirmed that the pathogenesis is a variety of reasons causing alveolar epithelial cells damage, which finally leads to the proliferation of fibroblasts and the aggregation of myofibroblasts to form fibroblast foci. Epithelial cell apoptosis may be an important factor in the early development of IPF. Factors such as inflammatory response, intracellular tension, and telomerase activity are involved in the apoptosis of alveolar epithelial cells and play an important role in the early stage of pulmonary fibrosis. An important pathological feature of IPF is the fibrotic foci formed by the active proliferation of fibroblasts. Fibroblast foci are the site of epithelial cell injury and repair. Various mediators secreted by epithelial cells after injury promote the migration, proliferation, and differentiation of fibroblasts, thereby causing extensive fibrosis in the alveoli and eventually progressive dyspnea. The pathogenesis of IPF may be caused by abnormal re-epithelialization and abnormal proliferation of fibroblasts after injury of alveolar epithelial cells. Cell death in IPF manifests as apoptosis following epithelial cell injury and plays an important role in disease development. Studies have confirmed that induction of lung epithelial cell apoptosis can lead to fibrosis in lung tissue. Alveolar epithelial cell injury as the initial factor in the development of pulmonary fibrosis is the most accepted theoretical hypothesis by scholars. Drugs targeting and reducting of alveolar epithelial cell apoptosis may provide new treatment options for preventing IPF. Studies have shown that aerobic glycolysis in lung tissue is closely related to pulmonary fibrosis. Hu et al (2020) found that the PFKFB3 inhibitor 3PO could reverse the significant upregulation of PFKFB3 expression and enhanced aerobic glycolysis in a mouse model of LPS-induced pulmonary fibrosis.

Pneumoconiosis

Pneumoconiosis is a systemic disease mainly caused by irreversible fibrosis of lung tissue caused by long-term inhalation of productive dust. At present, there is still no specific treatment for pneumoconiosis. In the pathological process of pulmonary fibrosis caused by dust, some alveolar epithelial cells are abnormally activated, and there are also damage and apoptosis. Disordered epithelial cell repair, release of pro-fibrotic factors, and epithelial-mesenchymal transition (EMT) promote the formation of fibroblast foci and myofibroblast foci and the production of a large amount of extracellular matrix, which eventually lead to the destruction of alveolar structure and the occurrence of pulmonary fibrosis.

Hyperoxia Lung Injury

Hyperoxia lung injury is an inflammatory lung disease based on diffuse lung cell damage which can rapidly affect gas exchange. Hyperoxia lung injury is a general term for acute and chronic non-injury, including pulmonary oxygen poisoning, that occurs when breathing high partial pressure oxygen with a volume fraction of 21% higher than normal pressure or hyperbaric oxygen higher than 1 absolute atmosphere. Due to the immature development of antioxidant enzyme system and pulmonary surfactant in newborns, especially premature infants, after high oxygen enters the lungs, oxygen free radicals are generated, causing cell damage, apoptosis, and necrosis, and at the same time producing inflammatory mediators and infiltration of inflammatory cells, which leads to pulmonary inflammatory response, tissue damage and abnormal repair. Hyperoxia causes oxidative damage to alveolar epithelial cells, which inhibits the process of alveolarization. Extensive damage to alveolar epithelial cells and the decline in their ability to repair damage significantly increase the permeability of the air-blood barrier, resulting in pulmonary edema, which promotes the occurrence of ALI.

Chronic Lung Disease in Premature Infants

Chronic lung disease (CLD) in premature infants is the most common and serious complication after prolonged inhalation of high concentrations of oxygen or mechanical ventilation or infection in premature infants. CLD in premature infants was first described by Northway in 1967 as a complication of the treatment of hyaline membrane disease in premature infants, also known as bronchopulmonary dysplasia (BPD). Oxygen therapy is one of the most commonly used treatments for premature infants with cardiopulmonary disease. Although this measure can change the hypoxic state of children and save their lives, long-term inhalation of high concentrations of oxygen can cause different degrees of lung damage, and severe cases can develop into CLD. With the widespread development of mechanical ventilation, the increasing improvement of management techniques for premature infants, and the widespread application of pulmonary surfactants, the survival rate of premature infants, especially extremely low birth weight (ELBW) infants (1000 g birth weight), has been significantly improved, but it is accompanied with increase in the incidence of chronic lung disease in premature infants, which has reached 30%-40% in foreign countries, and is in an upward trend in China. Due to the lack of effective monitoring and prevention methods, 10%-15% of CLD children die of respiratory failure due to severe pulmonary dysfunction, and the survivors also need to rely on oxygen or mechanical ventilation for a long time. Initial alveolar epithelial cell (AEC) damage and advanced pulmonary fibrosis are the main pathological features of CLD. At present, many attempts are made to effectively prevent CLD by reducing the degree of AEC damage or reducing the collagen deposition in lung tissue.

Chronic Obstructive Pulmonary Disease

Chronic obstructive pulmonary disease (COPD) is the leading cause of morbidity and mortality among respiratory diseases worldwide, and its incidence is still spreading. Smoking is known to be the main cause of COPD. Cigarette smoke (CS) is a complex mixture rich in oxidants. Among the various cell types that make up the lungs, alveolar epithelial cells are the main site of oxidative damage in CS. Studies have shown that the apoptosis index of alveolar epithelial cells in COPD patients is significantly higher than that of pulmonary vascular endothelial cells, and the two are positively correlated. The damage and apoptosis of endothelial cells first destroy the integrity of alveolar structure, and then damage or apoptosis of alveolar epithelial cells may occur. After endothelial cell injury or apoptosis, it may initiate and trigger apoptosis of other cells, especially alveolar epithelial cells, through direct cell-to-cell interaction and an indirect mechanism, thereby forming COPD and emphysema. In addition, COPD patients have vascular endothelial dysfunction, which is correlated with the severity of the disease. Vascular endothelial cell dysfunction is closely related to the occurrence and development of COPD. Inflammation, vascular injury, hemodynamic changes, hypoxia, oxidative stress, and apoptosis can promote vascular endothelial cell dysfunction. Studies have shown that vascular endothelial cell function is altered even in the early stages of COPD, even in healthy smokers with normal lung function. Abnormal changes in vascular endothelial cell function may play an important role in the occurrence and development of COPD and the high incidence of associated cardiovascular events.

Pneumocystis Disease

Pneumocystis disease is an interstitial pneumonia caused by pneumocystis (pneumocystis pneumonia, PCP). The main clinical manifestations are fever, dry cough, progressive dyspnea, etc., which cannot be relieved by oxygen alone, but can be quickly recovered after treatment for the causing factor. It mostly occurs in immunocompromised people, and the incidence in AIDS patients is as high as 70-80%. The virulence of pneumocystis is weak, and healthy people are mostly in recessive infection. Only when the host's immune function is low, the latent pneumocystis multiply, resulting in the occurrence of PCP. Inhalation of pneumocystis in the lower respiratory tract directly leads to damage and necrosis of type I alveolar epithelial cells, increased alveolar capillary permeability, and the alveoli are filled with pneumocystis and foamy eosinophils, reducing the surfactant in the alveoli and affecting gas exchange, causing hypoxemia (the most important feature of PCP patients). Compensatory hypertrophy of alveolar type II epithelial cells, and hyperplasia, hypertrophy, and partial shedding of alveolar space epithelial cells occur, simultaneously with proliferation of intrastromal macrophages and plasma cells, and interstitial fibrosis, resulting in severe lung dysfunction.

Pulmonary Embolism

Pulmonary embolism is a pathological process in which a sloughed thrombus or other material blocks the pulmonary artery or its branches, and is a common disease with high morbidity and mortality. Vascular endothelial cell injury is the first factor causing pulmonary embolism. Endothelial cells act on platelets and neutrophils through biomolecules such as microparticles and tissue factor, and participate in thrombosis. Since vascular endothelial cell injury and repair play an important role in the process of pulmonary embolism, in recent years, research on the occurrence and development mechanism of pulmonary embolism has increasingly focused on the explore in the molecular, cytological, and pathological aspects of endothelial cell injury and repair.

Cardiovascular Disease

The damage of vascular endothelial cells is related to the occurrence and development of many cardiovascular diseases, and thrombosis caused by vascular endothelial injury is the pathological basis of many cardiovascular diseases. The exfoliated vascular endothelial cells were earliestly found in the peripheral blood of patients with subacute endocarditis. With the deepening of research, it was found that the circulating endothelial cells of many cardiovascular diseases have different degrees of changes. Circulating endothelial cells are markedly increased in patients with acute myocardial infarction (AMI) and angina pectoris and persist for several days. The acute attack and exacerbation of coronary heart disease is due to functional changes after endothelial cell injury, and the degree of vascular endothelial cell injury is consistent with the severity of the disease. Studies in China have found that the circulating endothelial cells in AMI in ischemic heart disease increase significantly within 46 hours compared with normal people, and can last for 24 hours. Injury during reperfusion can also lead to increased circulating endothelial cells. When coronary heart disease is combined with other risk factors such as chronic heart failure (CHF), circulating endothelial cells can be significantly increased. Studies have found that the heavier the CHF, the more obvious the damage to the vascular endothelium, which in turn aggravates the disease. In addition, many studies have shown that the dysfunction caused by endothelial cell injury is closely related to hypertension. On the one hand, vascular endothelial dysfunction plays an important role in the occurrence and development of hypertension, and on the other hand, hypertension itself aggravates vascular endothelial dysfunction, forming a vicious circle. The endothelial cells of rats with hypertension were significantly increased in the blood of damaged organs. The circulating endothelial cells of patients with hypertension were significantly higher than those of normal people, and the increased number was higher than that of patients with coronary heart disease. Cardiovascular intervention is mainly to mechanically stimulate the vascular endothelium, resulting in injury. Different surgical procedures have different degrees of damage to the vascular endothelium. When vascular endothelial cells are damaged, endothelial dysfunction and hemodynamic changes are caused, resulting in the accumulation of a large number of inducers and vasoactive substances in the injured blood vessels, and platelet activation, which is the main pathophysiological mechanism of thrombosis in cardiovascular interventional surgery.

Diabetic Vascular Complication

Studies have confirmed that both chronic hyperglycemia and acute hyperglycemia can cause damage to endothelial function in humans and animals. Vascular endothelial dysfunction is an important cause of diabetic vascular complications (especially retinopathy, nephropathy, and impaired wound healing). Changes in vascular endothelial function are also important factors in other pathogenesis of diabetes, mainly reflected in insulin resistance, lipotoxicity and impaired insulin secretion. At present, it is believed that the damage of vascular endothelial function is the initiating factor and the main pathophysiological basis of diabetic vascular disease. Even diabetic patients who have not yet developed chronic vascular complications have significantly reduced endothelial function.

Cerebral Small Vessel Disease

Cerebral small vessels refer to small perforating arteries and small arteries (40~200 μm in diameter), capillaries, and small veins in the brain, which constitute the basic unit of blood supply to brain tissue and play an important role in maintaining brain function. The large and small vessels in the brain together constitute the vascular tree. They are structurally continuous, jointly affected by hemodynamics, and jointly exposed to risk factors. Therefore, the pathological changes of large and small vessels in the brain should theoretically have a parallel correlation in terms of severity. However, in clinical practice, an inconsistency is often found between these two kinds of vessels. For example, patients with severe cerebral small vessel disease but not complicated with large cerebral artery stenosis are often found, and vice versa.

Cerebral small vessel disease (CSVD) refers to syndromes of clinical, cognitive, imaging and pathological manifestations caused by various lesions of the small vessels. Traditionally, it refers to the clinical and imaging manifestations caused by small perforating artery and small artery lesions. CSVD mainly clinically manifests as stroke (deep small infarction, cerebral hemorrhage), cognitive and emotional disorders, and overall functional decline. In imaging, it manifests as lacunar infarction (LI), lacuna, white matter lesions (WML), enlarged perivascular space (EPVS) and cerebral microbleeds (CMB), etc.

Cerebral small vessel disease can involve arterioles, capillaries, and venules, with perforating arteries being the most common. Vascular endothelial cell injury, smooth muscle hyperplasia, and thickening of the basement membrane of the walls of small blood vessels caused by hypertension, vascular inflammation, or genetic defects can all cause chronic brain ischemia. Loss and hyperplasia of vascular smooth muscle cells, thickening of vascular walls, and stenosis of vascular lumen cause chronic, progressive local or even diffuse subclinical ischemia, demyelination of nerve cells, loss of oligodendrocytes, and axonal damage, resulting in incomplete ischemia. There are no clinical symptoms at this stage, and MRI shows white matter lesions. In addition, other research results suggest that the increase in vascular permeability after endothelial injury leads to extravasation of intravascular substances, causing damage to blood vessels and perivascular tissues, which may also play an important role in the progression of this stage of the disease.

In the present disclosure, the disease mediated by vascular endothelial cell injury comprises cerebral small vessel disease mediated by disruption or damage of the blood-brain barrier, but does not comprise cerebral microbleed, cerebral stroke and cerebral edema. In a particularly preferred embodiment of the invention, the cerebral small vessel disease mediated by blood-brain barrier disruption comprises white matter lesion. In a particularly preferred embodiment of the invention, the cerebral small vessel disease mediated by blood-brain barrier disruption manifests only as white matter lesion.

EXAMPLES

Example 1. YC-6 Significantly and Rapidly Inhibited the Up-Regulation of PFKFB3 Expression Caused by Glutamate Studies have shown that the increased expression of phosphofructokinase-2/fructose-2,6-bisphosphatase 3 (PFKFB3) and the accumulation of its downstream product lactate play a key role for the pathological damage in the development of acute lung injury, pulmonary arterial hypertension and other lung diseases. We analyzed the effect of YC-6 on the protein level of PFKFB3, the key molecule in lung injury. The results unexpectedly showed that YC-6 rapidly inhibited the upregulation of PFKFB3 protein expression and lactate accumulation, suggesting that this may be a unique mechanism of YC-6 in lung protection.

Culturing or Primary Cerebellar Granule Neuron

The cells were obtained from SD P7-8 neonatal mice. The cerebellum was taken, and the meninges and blood vessels were removed using microtweezers; the isolated cerebellar tissue was transferred to another dish containing dissection solution. The tissue was cut into pieces as small as possible using a tissue scissor. Digestion: The tissue in pieces was added into 7 mL of 0.25% trypsin digestive solution with a pipet, and was digested at 37° C. for 15 mins; the bench surface was cleaned and the instruments were washed. The container was turned upside down several times every five minutes to bring the tissue into better contact with the digestive solution. End of digestion: After the digestion, it can be seen that the tissue was sticked together and suspended in the liquid due to cell disruption and release of DNA. The digestion was terminated by adding 3 mL of RNase-containing 10% FBS DMEM medium. The container was turned upside down several times, and it can be observed that the remaining tissue dispersed due to DNA hydrolysis. Centrifugation was performed at 1000 rpm for 5 mins. As much supernatant as possible was carefully removed. Collection of single cell suspension: 7 mL of DNase-containing 10% FBS DMEM medium was taken with a pipet, by which the tissue pellet was gently pipeted. Rapid centrifugation was performed and stopped at the speed of 1500 rpm, and the single cell suspension was collected into a new 15 mL centrifuge tube. Cell Seeding: Centrifugation was performed at 1000 rpm for 5 minutes, then the cell pellet was collected, and the cells were resuspend in DMEM containing 10% FBS. The cells were counted with a hand-held cell counter, and the seeding density was 4.0-5.0×$10^5$ cells/mL. The seeding volume was 2 mL for 35 mm dishes and 300 μL for 48-well plates. Cell seeding and culturing: 24 hours after seeding, cytarabine (final concentration of 10 μM) was supplemented to inhibit the growth of glial cells. Glucose (5 mM) was supplemented on the seventh day to maintain nutrition. This was used on the eighth day. Glutamate-induced primary cerebellar granule neuron injury model and drug treatment.

Cell Treatment and Drug Administration

The culture medium of primary cerebellar granule neurons seeded in six-well plates was changed to 2 mL of kreb's buffer, and this was used as the normal control group. Glutamate with a final concentration of 200 μM was added for 5 mins and 15 mins, and this was used as the model group. Glutamate with the above concentrations was added for corresponding time after pre-incubation with 10 μM YC-6 or NMDA receptor blocker MK-801 for 20 mins, and this was used as the drug treatment group. Solvent HP-β-CD with the same amount as the drug treatment group was added in the solvent control group, and the pre-incubation time was the same as that of the drug treatment group.

Western Blot

SDS-polyacrylamide gel was prepared with a volume fraction of 12%, and the sample was loaded with a total amount of 20 μg of protein loaded in each well, and electrophoresis separation was performed under the condition of 100V constant voltage; then it was transferred to a PVDF membrane by wet transfer method. 5% nonfat milk powder was used for blocking at room temperature for 1 h; diluted primary antibody (antibody dilution solution was 3% BSA, antibody dilution ratio was 1:1000) was added, and incubation was performed overnight at 4° C.; TBST was used for washing for 3 times, 5 mins each time, and corresponding secondary antibody (antibody dilution solution was 3% BSA, antibody dilution ratio was 1:5000) was added, and incubation was performed at room temperature for 1 h, and TBST was used for washing for 3 times, 5 mins each time. Photos were taken by chemiluminescence color exposure.

YC-6 Significantly and Rapidly Inhibited Glutamate-Induced Up-Regulation of PFKFB3 Expression As shown in FIG. 1, glutamate stimulation led to a rapid up-regulation of intracellular PFKFB3 expression compared with the normal control group, and YC-6 treatment significantly inhibited this rapid increase.

Example 2. The Effect of YC-6 on the Key Metabolite Lactate in Lung Epithelial Injury Lactate, a product of anaerobic glycolysis, is downstream of the metabolic pathway in PFKFB3 regulation, and directly damages lung epithelial cells. Gong Y et al. demonstrated that LPS induced apoptosis, inflammatory cytokine production, enhanced glycolytic flux, and increased reactive oxygen species (ROS) in human alveolar epithelial A549 cells in vitro, and these changes were reversed by the PFKFB3 inhibitor 3PO. More importantly, lactate is also a key metabolite leading to lung injury, and lactate treatment of A549 cells resulted in apoptosis and enhanced ROS. These results suggest that anaerobic glycolysis may be an important factor in the apoptotic injury of lung epithelial cells in sepsis-related ALI. On the basis of YC-6 inhibiting the expression of PFKFB3, we further explored the effect of YC-6 on the lactate level in the downstream, which has the effect of lung epithelial cell injury. The results showed that YC-6 significantly inhibited the accumulation of lactate while inhibiting the key enzyme of glycolysis (PFKFB3). The reduction of lactate accumulation may be one of the mechanisms by which YC-6 attenuates lung epithelial cell injury.

Intracellular Lactate Assay

Pretreatment: The number of cells used for the determination of intracellular lactate content was 1-2*10^6. The specific experimental steps for cell pretreatment included the following. Cells was washed for three times with pre-cooled Kreb's buffer. 220 μL of cell lysate was added for complete lysis. After cell lysis, the lysate was collected into a 1.5 mL EP tube. Centrifugation was performed at 16,000 g for 5 mins at 4° C., 160 μL of supernatant was collected into a new EP tube, and the remaining supernatant was subjected to BCA protein quantification. 56 μL of 4 mM $HClO_4$ was added, and the tube was turned upside down to provide a sufficient mixing, and then put on ice for reaction for five minutes to remove the existing LDH in the sample to prevent endogenous interference. In this step, white protein precipitation should be observed at the bottom of the tube. Centrifugation was performed at 16,000 g for 5 mins at 4° C. 160 μL of the supernatant was collected and placed in a new EP tube. 68 μL of 2 mM KOH was added, and the tube was turned upside down to provide a sufficient mixing, and then put on ice for reaction for 5 mins. Centrifugation was performed at 16000 g at 4° C. for 15 mins, 160 μL of the supernatant was collected into a new EP tube, and centrifugation was performed again for 15 mins if there was white floc in the supernatant. The supernatant was diluted with cell lysate at a dilution factor of 600-800, and this dilution was used as the sample solution to be tested.

The method for determination of intracellular lactate content was performed according to the instructions of L-Lactate Assay Kit (abeam, ab65331). The specific steps were: 50 μL of the diluent was taken and added to a 96-well black-bottomed cell culture plate, then an equal volume of a substrate solution containing LDHA was added, the mixture was shaken and mixed well, and placed in a 37° C. carbon dioxide-free incubator and incubated for 30 mins. The fluorescence intensity was measured with a microplate reader in the dark and the excitation light wavelength was 535 nm. The fluorescence intensity read in the sample is brought into the standard curve of the fluorescence intensity corresponding to the lactate concentration of different standard products, and the fluorescence intensity was converted into the actual concentration of lactate in the sample solution.

YC-6 Significantly Inhibited Glutamate-Induced Intracellular Accumulation of Lactate, the End Product of Glycolysis Downstream of PFKFB3

Figure 2:
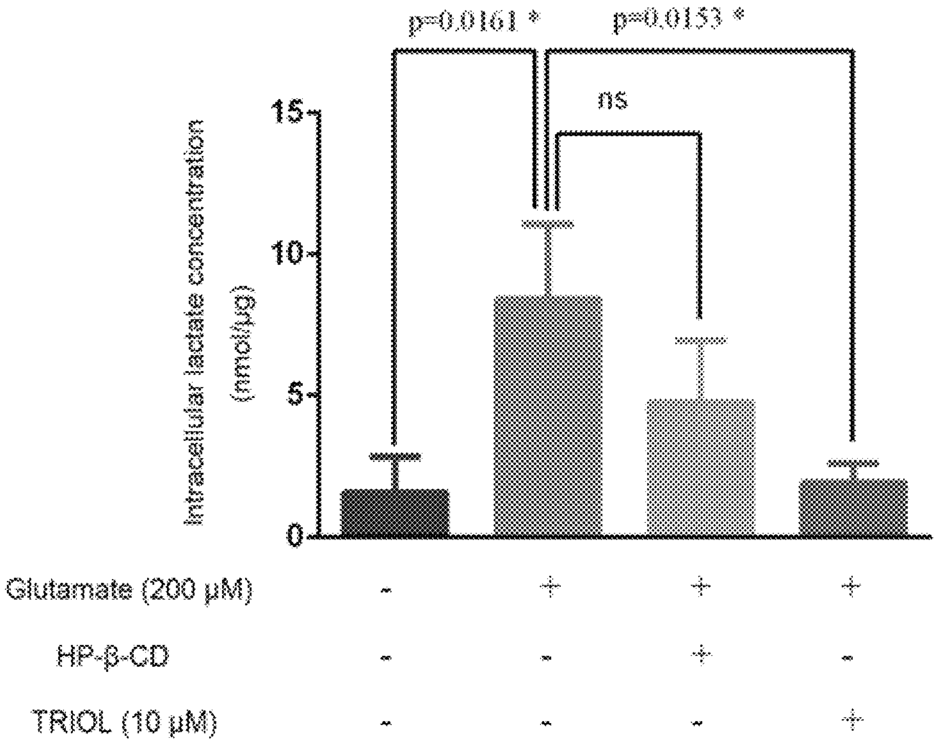
FIG. 2. YC-6 significantly inhibited glutamate-induced intracellular accumulation of lactate, the end product of glycolysis downstream of PFKFB3. The cultured primary neurons were stimulated with 200 μM glutamate for 15 mins. Pre-incubating with 10 μM YC-6 and the corresponding solvent HP-β-CD for 20 mins was performed in the experimental group, the solvent control group and the positive drug control group. The intracellular lactate content was measured after cell collection.

The primary cerebellar granule neuron cells were placed in 200 uM glutamate for stimulation for 15 mins, and the cell lysate was collected for studying the effect of YC-6 treatment on the glycolysis product lactate (FIG. 2). Intracellular lactate content was significantly increased with neurons stimulated with glutamate for 15 mins, and YC-6 treatment suppressed this increase. The above experimental results showed that YC-6 significantly inhibited the accumulation of lactate while inhibiting the key enzyme PFKFB3 of glycolysis.

Example 3. YC-6 Significantly Reduced Vascular Endothelial Cell Injury

Pulmonary vascular endothelial cells form the monolayer lining the vasculature, and their physiological location is exposed to direct stimuli such as bacterial endotoxins, LPS, inflammatory factors such as TNF-α, chemical toxicants, and oxidative stress, resulting in endothelial cell injury and apoptosis. Injury of pulmonary vascular endothelial cells leads to increased capillary permeability, resulting in increased pulmonary water content, resulting in pulmonary edema and dyspnea. At the same time, pulmonary vascular endothelial cells secrete and release various inflammatory mediators and cytokines, which make pro-inflammatory and anti-inflammatory mediators, coagulation and anticoagulation systems out of balance, cause pulmonary microcirculation disorders and pulmonary arterial hypertension, and can promote pulmonary interstitial edema, pulmonary hemorrhage, and progressive dyspnea, and patients develop progressive hypoxemia and respiratory distress. To evaluate whether YC-6 has a protective effect on vascular endothelial cell injury, an oxygen-glucose deprivation and restoration (OGD-R) injury model was used to evaluate the cell injury after prophylactic and therapeutic administration by detecting the release of cellular LDH. The results showed that YC-6 significantly reduced vascular endothelial cell injury in a dose-dependent manner, suggesting that YC-6 could play an effective protective role in the process of vascular endothelial cell-related lung injury caused by various pathological factors.

Cell Culturing

HUVEC cells were cultured in modified DMEM medium containing 10% fetal bovine serum. When the cells reached about 80% confluence, the cells were digested with 0.25% trypsin, and then pipetted evenly with modified DMEM containing 10% fetal bovine serum. The cell concentration was adjusted to $1\times10^5$ cells/mL, and the cells were seeded at 400 uL/well in a 24-well plate, and the experiment was carried out when the cells grew to about 70% confluence. RAOEC cells were cultured in high-glucose DMEM medium containing 10% fetal bovine serum, and the seeding conditions were the same as those for HUVECs.

Construction of OGD-R Injury Model

The hypoxia workstation was set to have an oxygen concentration of 1% (1% $O_2$, 5% $CO_2$, 94% $N_2$), a temperature of 37° C., and a humidity of 85%. A sugar-free DMEM medium was placed in the hypoxia workstation for pre-hypoxia for 3 hours. The medium in the culture plate was aspirated, and the plate was washed twice with preheated sugar-free DMEM medium, and 100 uL of sugar-free DMEM medium was added to each well. The culture plate was placed in the hypoxia workstation, and 300 uL of pre-hypoxic sugar-free DMEM medium was added to each well, and then the culture plate was placed in the hypoxia workstation for additional hypoxia for 4 hours. Restoration was then performed. The culture plate was taken out, and the sugar-free DMEM medium was replaced with 400 uL of normal medium containing 10% fetal bovine serum, and then the plate was placed in a 37° C. 5% $CO_2$ cell incubator for culturing for 24 hours. For the cells in the normal group, it was only replaced with 400 uL of new normal medium containing 10% fetal bovine serum.

Method of Administration

Prophylactic administration: cells were pre-coated with vehicle or drug (final concentration of 1 μM, 3 μM, 10 μM) for 1 hour before OGD treatment, and then corresponding vehicle or drug was added in the in sugar-free DMEM medium during OGD treatment. Corresponding vehicle or drug was added to the normal medium during restoration treatment until the end of the experiment. The model control group was not treated with any drug, and three replicates were performed in each treatment group.

Therapeutic administration: After the cells were treated with OGD, and at the same time of restoration, the vehicle or drug (final concentration of 1 μM, 3 μM, 10 μM) was administered until the end of the experiment. The model control group was not treated with any drug, and three replicates were performed in each treatment group.

Cell Injury Detection (LDH Detection)

At the end of the experiment, 50 uL of medium was taken from each well into a 96-well plate, and then cytotoxicity was detected according to the operating instructions of the LDH detection kit. The results were calculated as follows:

$$\text{Percent cytotoxicity} = 100\times\frac{\text{Experimental } LDH \text{ Release } (OD_{490})}{\text{Maximum } LDH \text{ Release } (OD_{490})}$$

The experimental results were statistically analyzed by one-way analysis of variance (One-way Anova), and Tukey's method was used for multiple comparisons, and $P<0.05$ was considered to have a significant statistical difference.

Experimental Results

Figure 3:
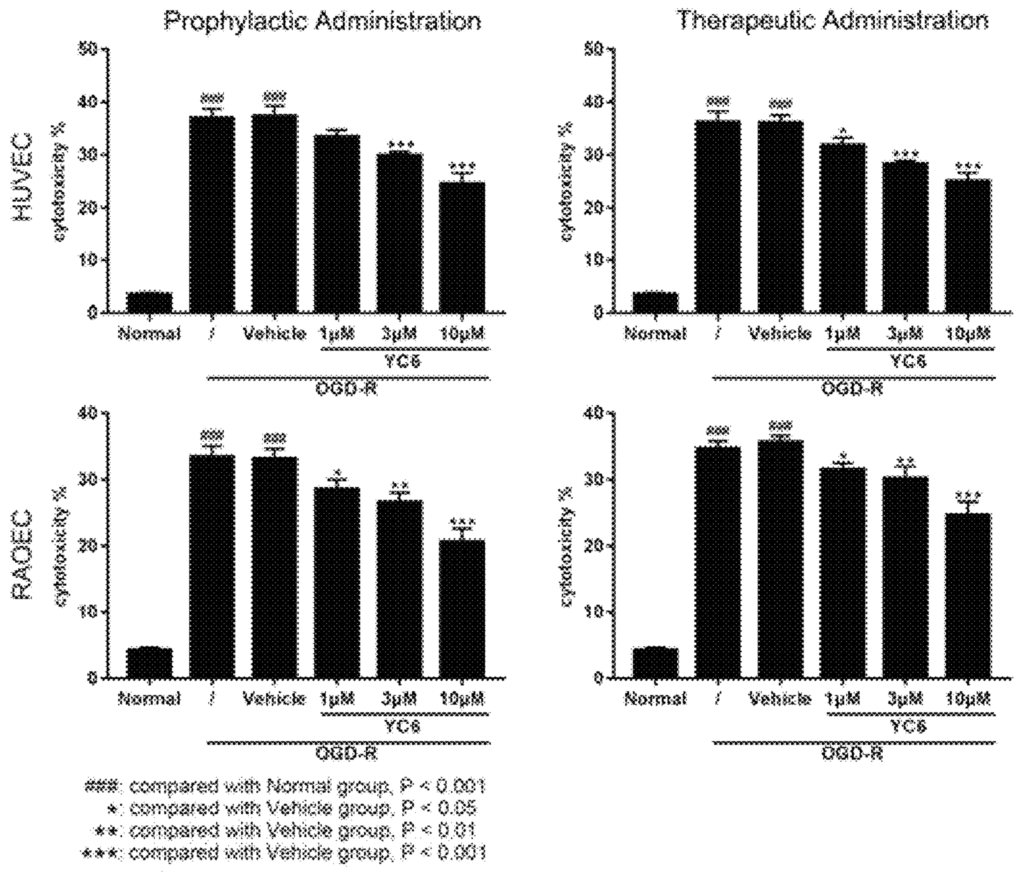
FIG. 3. YC-6 significantly reduced oxygen-glucose deprivation and restoration (OGD-R)-induced vascular endothelial cell injury. Human umbilical vein endothelial cells (HUVEC) and rat vascular endothelial cells (RAOEC) were subjected to oxygen-glucose deprivation (OGD) injury for 4 hours, and then restored to normal culture conditions for 24 hours before LDH detection and analysis. YC-6 prophylactically administered cells were pre-coated with vehicle (or solvent) or drugs (final concentrations of 1 μM, 3 μM, 10 μM) for 1 hour before OGD treatment, while therapeutic administration of the vehicle or YC-6 (final concentrations of 1 μM, 3 μM, 10 μM) was performed at the same time as restoration treatment.

As shown in FIG. 3, OGD-R treatment caused an increase in LDH release in human umbilical vein endothelial cells (HUVEC) and rat vascular endothelial cells (RAOEC), indicating that OGD-R injury treatment caused damage and death of HUVEC cells and RAOEC cells; YC-6 significantly reduced the OGD-R-induced increase in LDH release in a dose-dependent manner, and attenuated cell damage, regardless of whether it was administered prophylactically one hour before injury treatment or therapeutically administered during restoration treatment. YC-6 significantly reduced vascular endothelial cell injury in a dose-dependent manner, suggesting that YC-6 can play an effective protective role in the process of vascular endothelial cell-related lung injury caused by various pathological factors.

Example 4. YC-6 Reduced Hypoxia and LPS-Induced Alveolar Epithelial Cell Injury

Alveolar epithelial cells and capillary endothelial cells are the direct targets of various inflammation, toxic inhalation, viral infection, and sepsis and other damaging pathogenic factors. After injury, the permeability increases and apoptosis occurs, resulting in diffuse interpulmonary and alveolar edema, leading to progressive hypoxemia and respiratory distress. During the pathogenesis of COVID-19, lung epithelial cells are the main target of virus attack. SARS-CoV-2 (hereinafter referred to as CoV) is a single positive-stranded RNA virus with a length of about 27-32 kb. The viral genome is mainly composed of two parts: the replicase coding region and the structural protein coding region. Reports from the NIH team and others identified that the receptor for 2019-nCoV to enter human cells is ACE2. CoV specifically recognizes and invades human cells with rich expression of the angiotensin-converting enzyme 2 receptor (ACE2), especially respiratory epithelial cells and alveolar cells, so it is easy to infect and spread in the lower respiratory tract, causing pneumonia. However, it can be observed clinically that after the virus test turns negative, pulmonary inflammation can still exist or even worsen, and antiviral treatment alone cannot save the lives of many severely and critically ill patients. Lung epithelial cells (HPAEpiC) include all two types of alveolar epithelial cells of type I or II. In order to evaluate whether YC-6 has a protective effect on lung epithelial cells (HPAEpiC) directly, in this section, bacterial lipopolysaccharide (LPS) and hypoxia injury models were used to evaluate the protective effect of YC-6 on lung epithelial cells by detecting the release of LDH in cells, and to provide experimental evidence for YC-6 in the treatment of ARDS caused by different factors including SARS-CoV-2. The experimental results showed that YC-6 significantly reduced the damage of alveolar epithelial cells induced by hypoxia and LPS in a dose-dependent manner.

Cell Culturing

HPAEpiC cells were cultured with alveolar epithelial cell medium. When the cells grew to about 80% confluence, the cells were digested with 0.25% trypsin, and then pipetted evenly with alveolar epithelial cell medium. The cell concentration was adjusted to $2\times10^5$ cells/mL, and the cells were seeded in a 24-well plate at 400 uL/well. The experiment was conducted when the cells grew to about 70% confluence.

Construction of LPS+Hypoxia Model

The hypoxia workstation was set to have an oxygen concentration of 1% (1% $O_2$, 5% $CO_2$, 94% a temperature to 37° C., and a humidity of 85%. After the conditions in the hypoxia workstation were stable, 1 mg/mL LPS was directly added to the cells to make the final concentration of LPS 20 mg/mL, and then the cells were cultured in the hypoxia workstation for 24 hours.

Method of Administration

Before being subjected to the model, the cells in the drug group were pre-incubated with vehicle (20% hydroxypropyl cyclodextrin solution) or drug (the final concentration of YC-6 was 1 μM, 5 μM, 10 μM) for 1 hour, and then added with LPS, and placed in the hypoxia workstation for constructing the model, until the end of the experiment. The model control group was not treated with any drug, and the normal group was placed in a cell incubator for routine culturing. 10 μM dexamethasone was used as the drug control. Three replicates were performed for each treatment group.

Experimental Results

Figure 4:
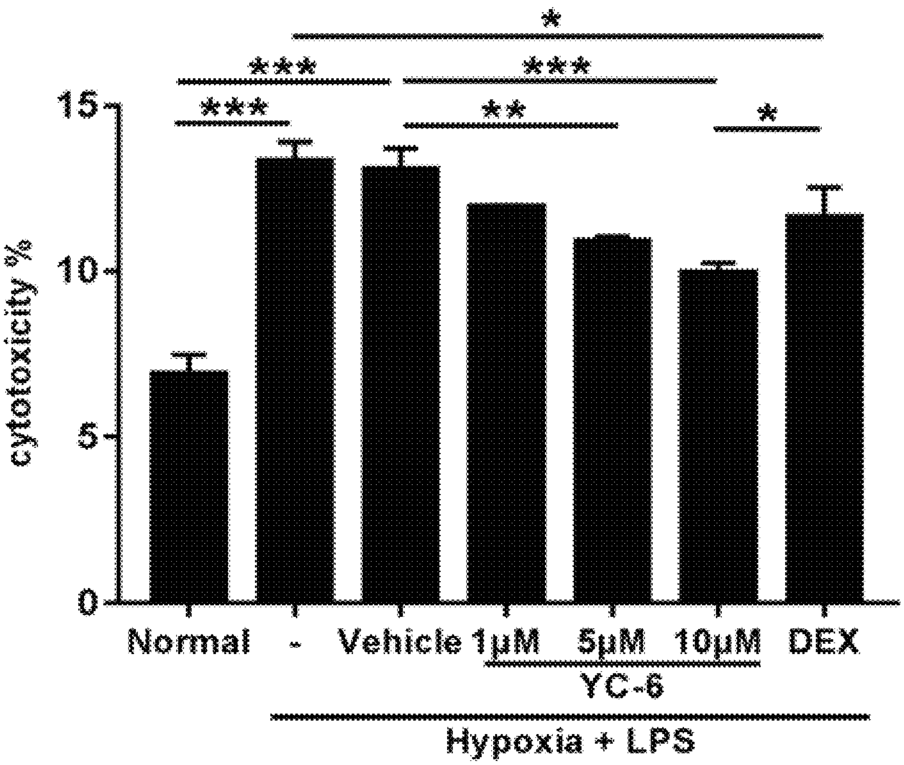
FIG. 4. YC-6 significantly reduced hypoxia and LPS-induced damage to human alveolar epithelial cells. The final concentrations of YC-6 for pre-incubation were 1 μM, 5 μM, and 10 μM, 10 μM dexamethasone was added in the drug control, and the corresponding volume of 20% hydroxypropyl cyclodextrin was added in the vehicle control. After 1 hour pre-incubation, the cells were subjected to 20 μg/mL LPS and 1% $O_2$ hypoxia treatment for 24 hours.

The experimental results are shown in FIG. 4. Hypoxia and LPS stimulation caused an increase in the release of LDH from human alveolar epithelial cells, indicating that hypoxia and LPS treatment caused damage to human alveolar epithelial cells, while YC-6 could dose-dependently reduce damage to alveolar epithelial cells induced by hypoxia and LPS stimulation. Dexamethasone at 10 μM also significantly attenuated this damage, and YC-6 at 10 μM had a significantly better protective effect than dexamethasone. The above results indicated that YC-6 could significantly reduce the damage of alveolar epithelial cells induced by hypoxia and LPS stimulation in a dose-dependent manner.

Example 5. YC-6 Significantly Improved LPS-Induced Acute Lung Injury in Rats

Animal Grouping and Drug Administration

Animal grouping: 60 qualified rats with uniform body weight were selected and included in the experiment, and were randomly divided into 6 groups according to body weight, 10 rats/group. The animal grouping and the drug treatment dose of each group were as follows:

| Group | Treatment |
|---|---|
| Normal control group | No treatment |
| LPS model group | LPS (6.4 mg/kg) + 20% HP-β-CD |
| Low-dose drug model group | LPS (6.4 mg/kg) + YC-6 (12 mg/kg/d) |
| Medium-dose drug model group | LPS (6.4 mg/kg) + YC-6 (40 mg/kg/d) |
| High-dose drug model group | LPS (6.4 mg/kg) + YC-6 (120 mg/kg/d) |
| Positive drug model group | LPS (6.4 mg/kg) + HC (50 mg/kg/d) |

Drug administration: Test drugs were administered by tail vein at 0.3 mL/100 g body weight, hydrocortisone (25 mg/kg) was administered intraperitoneally at 0.5 mL/100 g body weight; the first administration for all the test agents were performed 0.5 h before LPS administration in the model. The test drug solvent and YC-6 were intravenously injected once every 6 h for a total of 4 injections, and the hydrocortisone (HC) group was intraperitoneally injected once every 12 h for a total of 2 injections.

Method of Constructing the Model

After the rats were weighed and anesthetized by isoflurane, they were fixed in a supine position. The hair in the skin of the neck was removed, the skin of the neck was sterilized with 75% ethanol, and incised in the middle, after which the subcutaneous tissue was bluntly separated, and the upper trachea was exposed. 8 mg/mL LPS solution was injected into the trachea with a syringe, 0.2 mL/rat, and each rat was calculated as having body weight of 250 mg, and the dose was 6.4 mg/kg. Immediately after injection, the rats were erected, shaken, and rotated to distribute the LPS solution evenly in the lungs. The skin was sutured and disinfected with iodophor.

Lung Tissue Processing 24 h after LPS injection, the animals were anesthetized by intraperitoneal injection of 20% ulose solution at a volume of 6 mL/kg body weight. After the abdominal aorta was bled till the animal was dead, the thoracic cavity was exposed, and the lung tissue was collected. The left lung was fixed in 10% paraformaldehyde solution for 48 hours, after which the coronal plane of the left lung was cross-sectioned into two equal-width upper and lower parts, and then the lower half of the left lung was cross-sectioned into two equal-width parts according to the coronal plane. The sagittal plane of the upper half of the left lung and the coronal plane of the two lower half of the left lung were embedded in a paraffin block, sectioned and stained with hematoxylin-eosin (HE).

Histochemical HE Staining

Tissue dehydration and paraffin embedding: The tissue was taken out of the fixative and successively immersed in 50% ethanol (30 min)-70% ethanol (overnight)-80% ethanol (30 min)-90% ethanol (30 min)-95% ethanol (30 min)-absolute ethanol (2 times, 30 min each time)-xylene (2 times, 5~10 min each time, until the sample was completely transparent)-62° C. paraffin (3 times, 1 hour each time), followed by tissue embedding. Tissue paraffin sectioning: The thickness was 3 μm, the sections were dried on a microtome, and then placed in a 37° C. oven to dry overnight, and then used for HE staining. HE staining: The paraffin sections stored at room temperature were taken out, baken in a 65° C. oven for 30 min, and then immediately immersed in xylene for three times for deparaffinization, 5 min, 2 min, and 2 min respectively; Rehydration: After being immersed in xylene for the third time, the sections were successively immersed in 100% ethanol-100% ethanol-95% ethanol-90% ethanol-80% ethanol-70% ethanol-50% ethanol-distilled water for rehydration, each time for 1 min; the sections were taken out to dry slightly, then placed in a wet box, and hematoxylin solution was added to the tissue to ensure that the tissue was completely covered by the staining solution, and incubation was performed at room temperature for 5 min; the sections was rinsed gently with distilled water to remove excess hematoxylin, and then put back into the wet box, and eosin solution was added to the tissue, and incubation was performed for 2 min at room temperature; the sections was rinsed gently with distilled water; the sections were successively immersed in 90% ethanol (1 min)-95% ethanol (1 min)-100% ethanol (1 min)-100% ethanol (1 min)-xylene (5 min)-xylene (5 min) for dehydration for transparency, and then neutral resin (diluted with an appropriate amount of xylene, about 50% xylene) was used to cover the sections.

Pathological Observation and Scoring of Lung Tissue

Pathological observation of lung tissue: The pathological changes of lung tissue were observed under light microscope with Nikon Eclipse Ti-U inverted fluorescence microscope. Analyses were performed by grade of changes in inflammatory cell infiltration, alveolar hemorrhage, alveolar wall thickening, alveolar dilation, and bronchial epithelial shedding. Lung injury was scored according to the Smith scoring system. Lung injury severity was scored by two experimenters who were unaware of the experimental grouping and dosing information, including inflammatory cell infiltration, alveolar hemorrhage, alveolar wall thickening, alveolar dilation, and bronchial epithelial shedding. 0 point: normal; 1 point: mild lesions, the scope of lesions is less than 25% of the entire visual field area; 2 points: moderate lesions, the scope of lesions is 25%-50% of the entire visual field area; 3 points: severe lesions, the scope of lesions is 50%-75% of the entire visual field area; 4 points: very severe lesions, the lesion range is greater than 75% of the entire visual field area. The total lung injury pathology score was the sum of the above scores.

Experimental Results

Figure 5:
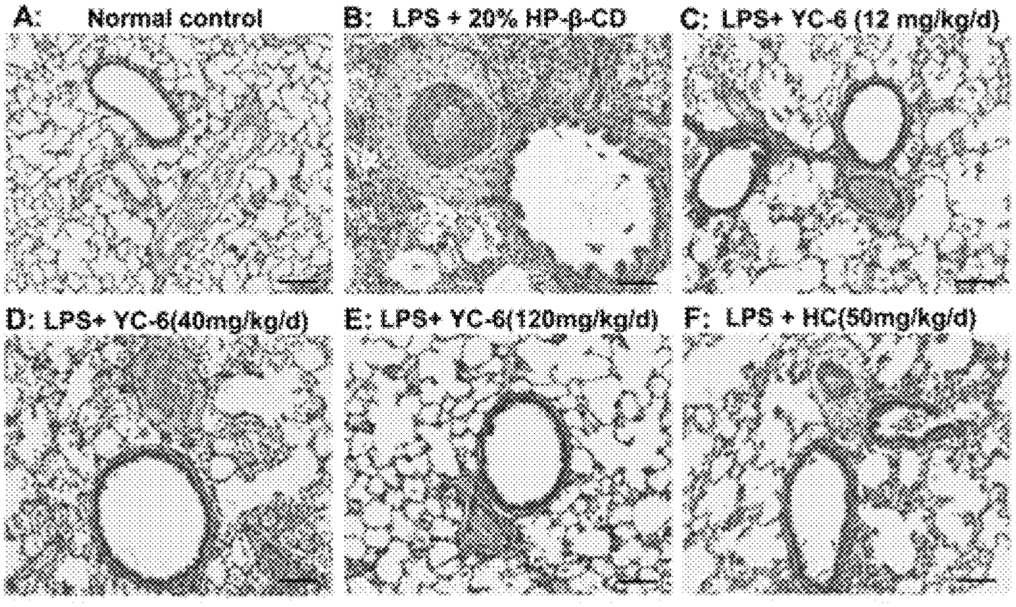
FIG. 5. YC-6 protected the pathological effects of LPS-induced acute lung injury. Red arrow indicates alveolar and pulmonary interstitial edema, blue arrow indicates peripheral loose lesion tissue, yellow arrow indicates inflammatory cell infiltration, green arrow indicates bronchial mucosal epithelial damage and shedding, and orange arrow indicates alveolar congestion. The black bar represents 100 μm.

As shown in the pathological observation results in FIG. 5, in the normal control group (FIG. 5A), the lung tissue structure of the rats was clear, the alveolar structure was polygonal or circular thin-walled vacuoles, the alveolar space was clean, the boundary was clear, the alveolar wall was not thickened, and there was no inflammatory infiltration in the interstitium; the structure of the bronchial wall was clear, and no epithelial cell shedding was seen; the blood vessels were normal. In the LPS model group (FIG. 5B), in rat lung tissue, massive inflammatory cell infiltration (yellow arrow), alveolar space and interstitial edema, with severe fibrous exudation (red arrow), alveolar wall thickening, alveolar expansion and collapse; bronchial mucosal epithelial sloughing (green arrow); alveolar congestion, and a large number of red blood cells (orange arrow) in the alveoli; loose tissue around the pulmonary blood vessels with obvious exudation (blue arrow) were seen, indicating that LPS caused increased pulmonary vascular permeability. Compared with the LPS model group, the YC-6 group with different doses (FIG. 5C-E) showed reduced inflammatory cell infiltration, reduced alveolar damage, and increased vascular barrier permeability; pathological results showed that YC-6 could significantly improve LPS-induced acute lung injury.

Figure 6:
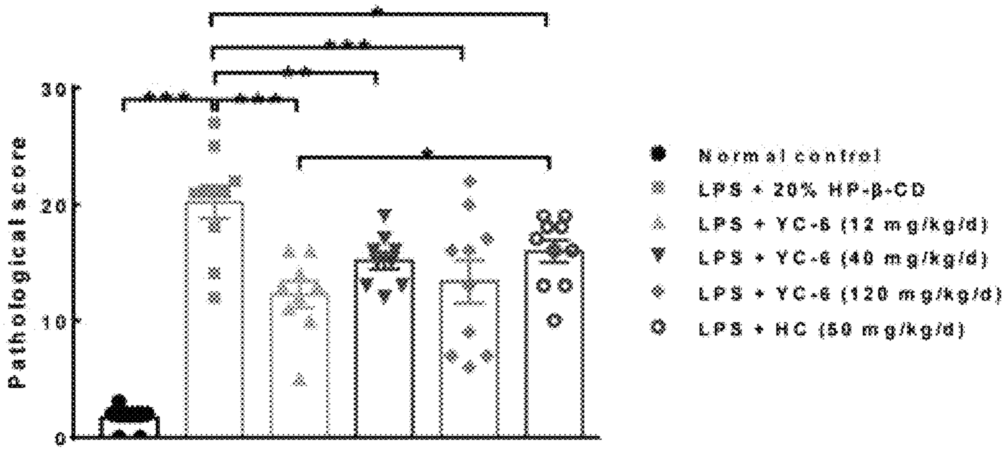
FIG. 6. YC-6 significantly reduced the pathological score of LPS-induced acute lung injury in rats. n=9-10; *: p<0.05; : p<0.01; *: p<0.001.

As shown in the statistical results of lung injury pathological score in FIG. 6, the scores of the LPS model group were significantly higher than those of the normal control group ($P<0.001$). Compared with the LPS model group, the YC-6 treatment group at doses of 12, 40, and 120 mg/kg/d had significantly lower pathological scores ($P<0.01$ or $P<0.001$); and the treatment of YC-6 in the low-dose group provided significantly better protective effect than that of 50 mg/kg/d hydrocortisone ($P<0.05$).

These results suggest that LPS caused significant lung injury, manifested as massive inflammatory cell infiltration, alveolar wall thickening, alveolar congestion, dilation and collapse, and bronchial mucosal epithelial shedding. YC-6 significantly reduced LPS-induced increase in vascular endothelial barrier permeability, reduced inflammatory cell infiltration, and attenuated alveolar damage.

Example 6. YC-6 Alleviated Acute Lung Injury in *Macaca fascicularis*

Non-human primates are closer to humans in terms of phylogeny and anatomical structure, which can reduce the deviation of drug efficacy evaluation caused by species differences; at the same time, the research data such as the pharmacological dose, toxicology and drug efficacy obtained in non-human primates can provide a more reliable basis for subsequent clinical trials. We established a lung injury model of acute hypobaric hypoxia in *Macaca fascicularis* using non-human primate *Macaca fascicularis* and a high-altitude decompression chamber. Pathological and biochemical tests such as HE staining were used to evaluate whether YC-6 alleviates lung injury caused by acute hypobaric hypoxia.

Grouping of Experimental Animals

Twenty-four healthy male *Macaca fascicularis,* 6 to 6.5 years-old, weighted 6.5-7.5 kg, were purchased from Kangda Laboratory Animal Center, Gaoyao City, Guangdong, China, in which 17 male *Macaca fascicularis* were divided into 3 groups, as shown in the following table:

| Group | Treatment |
|---|---|
| Normal control group (Normobaric Normoxia, NN) | Normobaric normoxia control group (n = 6) |
| Acute hypobaric hypoxia group (Acute Hypobaric Hypoxia. HH) | Glucose saline + acute hypobaric hypoxia treatment (n = 5) |
| Drug treatment group (HH + YC-6) | Glucose saline and YC-6 (100 mg/kg/two days) + acute hypobaric hypoxia treatment (n = 6) |

Construction of Model of Acute Hypobaric Hypoxic Lung Injury in *Macaca Fascicularis* Induced by Simulation of 7500 Meters of Altitude in a Low-Pressure Chamber Three *Macaca fascicularis* housed in the animal room were randomly selected each time. For each animal, 10 ml of blood was collected, and 10 ml of glucose normal saline was injected intravenously, and marked. The animals were then housed in a low-pressure chamber for 1 day to acclimate to the experimental environment. In the acute hypobaric hypoxia group, the altitude was simulated to 3000 meters at a speed of 3 m/s; after the animals stayed in the low-pressure chamber at a simulated altitude of 3000 meters for 30 minutes, 10 ml of blood was taken from each animal and 10 ml of glucose saline was injected intravenously; the altitude was then simulated to 4500 meters at a speed of 3 m/s; after the animals stayed in the low-pressure chamber at a simulated altitude of 4500 meters for 30 minutes, 10 ml of blood was taken from each animal and 10 ml of glucose saline was injected intravenously; the altitude was simulated to 6000 meters at a speed of 3 m/s; after the animals stayed in the low-pressure chamber at a simulated altitude of 6000 meters for 30 minutes, 10 ml of blood was taken from each animal and 10 ml of glucose saline was injected intravenously; the altitude was simulated to 7500 meters at a speed of 2 m/s; after the animals stayed at a simulated altitude of 7500 meters in the low-pressure chamber for 24 hours, the altitude was lowered to 6000 meters at a speed of 3 m/s, and 10 ml of blood was taken from each animal and 10 ml of glucose saline was injected intravenously; the altitude was simulated to 7500 meters at a speed of 2 m/s; after staying at 7500 meters for 48 hours, the altitude was lowered to 6000 meters at a speed of 3 m/s, the animals were anesthetized (0.06 ml/kg ketamine hydrochloride injection, 0.02 ml/kg xylazine hydrochloride injection), and sacrificed by carotid bloodletting, and dissected and subject to sampling, and the samples were then fixed. The *Macaca fascicularis* in the normobaric normoxia control group were anesthetized (0.06 ml/kg ketamine hydrochloride injection, 0.02 ml/kg xylazine hydrochloride injection) in the plain (an altitude of 352 meters), then sacrificed by carotid bloodletting, and dissected and subject to sampling, and the samples were then fixed.

Time, Dosage and Method of Administration

In the drug treatment group, before the simulated elevation of the altitude, YC-6 solution was diluted to 10 ml with glucose saline, and intravenously injected to the animals at a dose of 10 mg/kg; for the animals in the acute hypobaric hypoxia group, only 10 ml of glucose saline was intravenously injected. After staying for 30 minutes at a simulated height of 3000 meters in the low-pressure chamber, in the drug treatment group, YC-6 solution was diluted to 10 ml with glucose saline, and intravenously injected to the animals at a dose of 10 mg/kg; for the animals in the acute hypobaric hypoxia group, only 10 ml of glucose saline was intravenously injected. After staying for 30 minutes at a simulated height of 4500 meters in the low-pressure chamber, in the drug treatment group, YC-6 solution was diluted to 10 ml with glucose saline, and intravenously injected to the animals at a dose of 10 mg/kg; for the animals in the acute hypobaric hypoxia group, only 10 ml of glucose saline was intravenously injected. After staying for 30 minutes at a simulated height of 6000 meters in the low-pressure chamber, in the drug treatment group, YC-6 sustained-release formulation was divided into 5 parts for skeletal muscle intramuscular injection at a dose of 30 mg/kg; for the animals in the acute hypobaric hypoxia group, only 10 ml of glucose saline was injected intravenously. After staying for 24 hours at a simulated height of 7500 meters in the low-pressure chamber, in the drug treatment group, YC-6 solution was diluted to 10 ml with glucose saline and intravenously injected to the animals at a dose of 10 mg/kg, and YC-6 sustained-release formulation was divided into 5 parts for skeletal muscle intramuscular injection at a dose of 30 mg/kg. For the animals in the acute hypobaric hypoxia group, only 10 ml of glucose saline was injected intravenously. After staying at 7500 meters for 48 hours, the altitude was lowered to 6000 meters at a speed of 3 m/s, the animals were anesthetized (0.06 ml/kg ketamine hydrochloride injection, 0.02 ml/kg xylazine hydrochloride injection), and sacrificed by carotid bloodletting, and dissected and subject to sampling, and the samples were then fixed. The *Macaca fascicularis* in the normobaric normoxia control group were anesthetized (0.06 ml/kg ketamine hydrochloride injection, 0.02 ml/kg xylazine hydrochloride injection) in the plain (an altitude of 320 meters), then sacrificed by carotid bloodletting, and dissected and subject to sampling, and the samples were then fixed.

Tissue Paraffin Embedding, Sectioning, and Hematoxylin-Eosin (HE) Staining

Tissue paraffin embedding and fixation: After the lung tissue was collected, the lung tissue was trimmed into a tissue block with a thickness of no more than 1 cm, and then placed in 10 times the volume of paraformaldehyde for fixation. During fixation, floating lung tissue was pressed down below the liquid surface with cotton to fully fix the tissue. After 48 hours, the fixative solution was replaced and fixation was continued for 48 hours, and then it can be used for paraffin embedding. The tissue was taken out of the fixative and successively immersed in 50% ethanol (30 min)-70% ethanol (overnight)-80% ethanol (30 min)-90% ethanol (30 min)-95% ethanol (30 min)-absolute ethanol (2 times, 30 min each time) xylene (2 times, 5-10 min each time, until the sample was completely transparent)-62° C. paraffin (3 times, 1 hour each time), followed by tissue embedding. Tissue paraffin sectioning: The thickness was 3 μm, the sections were dried on a microtome, and then placed in a 37° C. oven to dry overnight, and then used for HE staining. Hematoxylin-eosin (HE) staining: The paraffin sections stored at room temperature were taken out, baken in a 65° C. oven for 30 min, and then immediately immersed in xylene for three times for deparaffinization, 5 min, 2 min, and 2 min respectively; Rehydration: After being immersed in xylene for the third time, the sections were successively immersed in 100% ethanol-100% ethanol-95% ethanol-90% ethanol-80% ethanol-70% ethanol-50% ethanol-distilled water for rehydration, each time for 1 min; the sections were taken out to dry slightly, then placed in a wet box, and hematoxylin solution was added to the tissue to ensure that the tissue was completely covered by the staining solution, and incubation was performed at room temperature for 5 min; the sections was rinsed gently with distilled water to remove excess hematoxylin, and then put back into the wet box, and eosin solution was added to the tissue, and incubation was performed for 2 min at room temperature; the sections was rinsed gently with distilled water to remove excess eosin, then gently rinsed twice with the color-enhancing solution provided with the kit, and then slightly rinsed with distilled water; the sections were successively immersed in 90% ethanol (1 min)-95% ethanol (1 min)-100% ethanol (1 min)-100% ethanol (1 min)-xylene (5 min)-xylene (5 min) for dehydration for transparency, and then neutral resin (diluted with an appropriate amount of xylene, about 50% xylene) was used to cover the sections.

Figure 7:
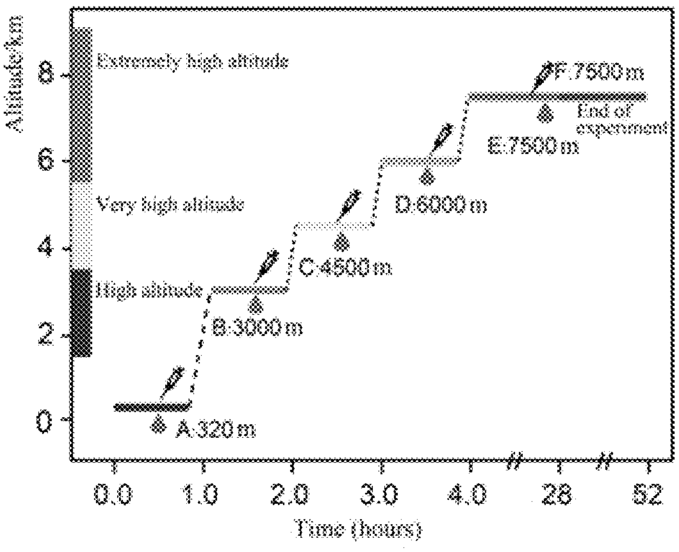
FIG. 7. The process of constructing a model of acute hypobaric hypoxia-induced lung injury in *Macaca fascicularis*. After hypoxia treatment at 320 meters (A), 3000 meters (B), 4500 meters (C), 6000 meters (D), 7500 meters for 24 hours (E) and 7500 meters for 48 hours (F) and drug administration, the lung samples of *Macaca fasciculari* were finally collected. Syringes show the time points of drug administration.

Effect of YC-6 on Pulmonary Vascular Congestion and Swelling and Thickening of Alveolar Septa As shown in the model established in FIG. 7, as altitude rised, *Macaca fascicularis* showed significant symptoms of acute altitude sickness, such as shortness of breath, vomiting, ataxia, confusion, etc., indicating a successful replication of the model of acute altitude sickness in a non-human primate *Macaca fascicularis*. The early pathological features of ALI/ARDS are alveolar wall telangiectasia, widening of alveolar septa, and exudation of serous fluid, neutrophils, and macrophages in the alveolar cavity, and then develops into diffuse lung congestion, edema, and alveolar hyaline membrane formation and focal lung collapse. In this study, HE staining was used to observe whether YC-6 alleviates lung injury caused by acute hypobaric hypoxia.

Figure 8:
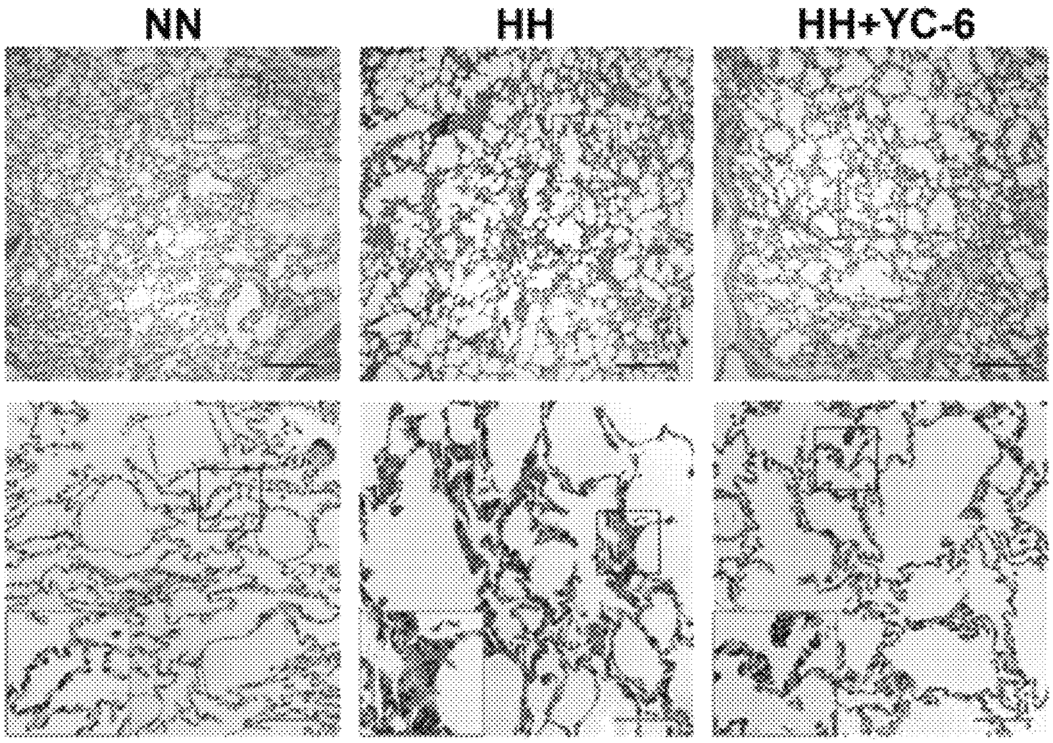
FIG. 8. YC-6 inhibited acute hypobaric hypoxia-induced pulmonary vascular congestion and alveolar septal thickening in *Macaca fasciculari*. Normobaric normoxia group (Normobaric normoxia, NN); acute hypobaric hypoxia group (Hypobaric hypoxia, HH); YC-6 treatment group (HH+YC-6). The red arrows indicate the vascular cross-section of the congested and swollen lung tissue. The second row of images are enlarged images of the area in the blue frames of the first row of images, and the red frames in the second row of images are further enlarged images of the area in the black frames. The black bar represents 500 μm and the red bar represents 100 μm.
Figure 9:
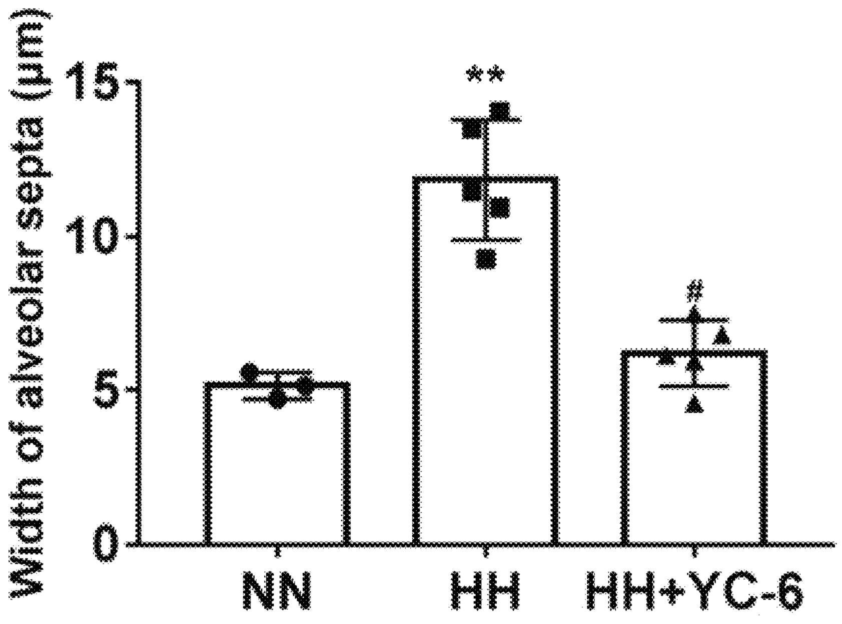
FIG. 9. Statistical analysis of YC-6 significantly inhibiting acute hypobaric hypoxia-induced alveolar septal thickening in *Macaca fasciculari*, NN (Normobaric normoxia): normobaric normoxia group, n=3; HH (Hypobaric hypoxia): acute hypobaric hypoxia group, n=5; HH+YC-6: YC-6 treatment group, n=5; **: compared with NN, p<0.01; #: compared with HH group, p<0.05.

As shown in FIG. 8, in the normal control group, the alveolar structure of the lung tissue of the *Macaca fascicularis* was polygonal or circular thin-walled vacuoles with clear boundaries, thin-walled alveolar septa presented between alveolar epithelial cells, and capillary cross-sections were visible in the septa. As shown in the results in FIG. 8, acute hypobaric hypoxia caused a significant thickening of the alveolar septum; however, it was significantly improved after YC-6 administration. The thickness of alveolar septum was measured in each group and the statistics showed (FIG. 9) that YC-6 significantly reduced the alveolar septal thickening injury. The above results show that YC-6 can effectively reduce the thickening of the alveolar septum caused by acute hypobaric hypoxia, suggesting that YC-6 maintains the normal tissue structure and function of pulmonary blood vessels and alveoli, reduces the permeability damage of the air-blood barrier, and is expected to have a therapeutic effect on lung injury diseases such as COVID-19.

Figure 10:
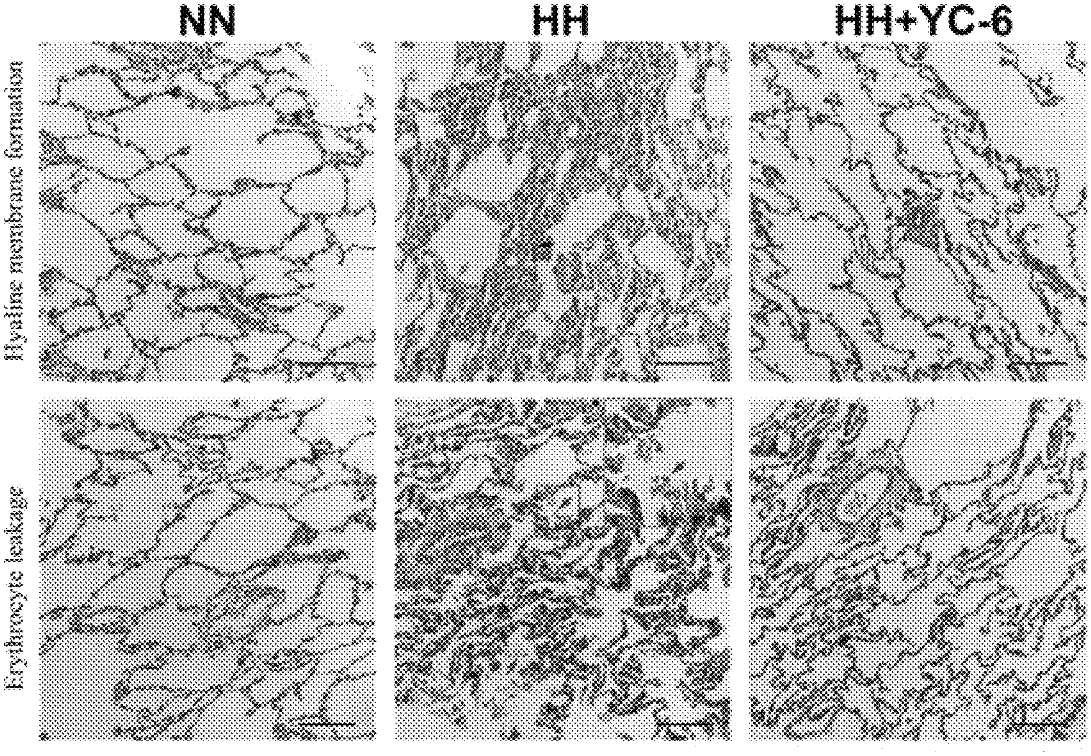
FIG. 10. YC-6 inhibited acute hypobaric hypoxia-induced hyaline membrane formation and erythrocyte leakage in *Macaca fasciculari*. NN (Normobaric normoxia): normobaric normoxia group; HH (Hypobaric hypoxia): acute hypobaric hypoxia group; HH+YC-6: YC-6 treatment group. Red arrows indicate protein hyaline membranes in the alveolar space, black arrows indicate fibrous hyperplasia of the alveolar septa, and blue arrows indicate erythrocytes in the alveolar space. The black bar represents 100 μm.

Effect of YC-6 on Protein Hyaline Membrane Formation in the Alveolar Space and Erythrocyte Leakage It has been reported that one of the hallmark pathological changes of acute lung injury in humans is diffuse alveolar damage (DAD). One of the important characteristic manifestations of diffuse alveolar damage is the change of alveolar permeability, which leads to the entry of blood proteins into the alveoli and the formation of a hyaline membrane formed by protein deposition[8]. At the same time, the formation of hyaline membrane is also one of the characteristic pathologies of ARDS, which was found in the pathological examination of patients with COVID-19[1]. The hyaline membrane is a layer of uniform red-stained membrane formed on the surface of respiratory bronchioles, alveolar ducts, and alveoli, which is composed of exuded plasma protein, cellulose and disintegrated alveolar epithelial cell debris. The formation of hyaline membrane and the fibrous proliferation of alveolar interstitium increase the alveolar septum, which leads to the decrease of the permeability of the alveolar membrane and causes the dysfunction of blood gas exchange. As shown in FIG. 10, acute hypobaric hypoxia caused fibrous hyperplasia of alveolar septa (black arrows), and at the same time caused the formation of protein hyaline membranes in part of alveolar spaces (red arrows), indicating that acute hypobaric hypoxia caused diffuse alveolar damage; acute hypobaric hypoxia also caused the leakage of erythrocytes into the alveolar space (blue arrows), indicating that acute hypobaric hypoxia caused the destruction of the air-blood barrier; however, no such obvious changes were observed in the YC-6 treatment group, suggesting that YC-6 had a protective effect on alveolar epithelial cells and vascular endothelial cells. The above results suggest that YC-6 may protect alveolar epithelial cells and vascular endothelial cells, reduce the increase in the permeability of the air-blood barrier caused by acute hypobaric hypoxia, and maintain normal structure and function.

Figure 11:
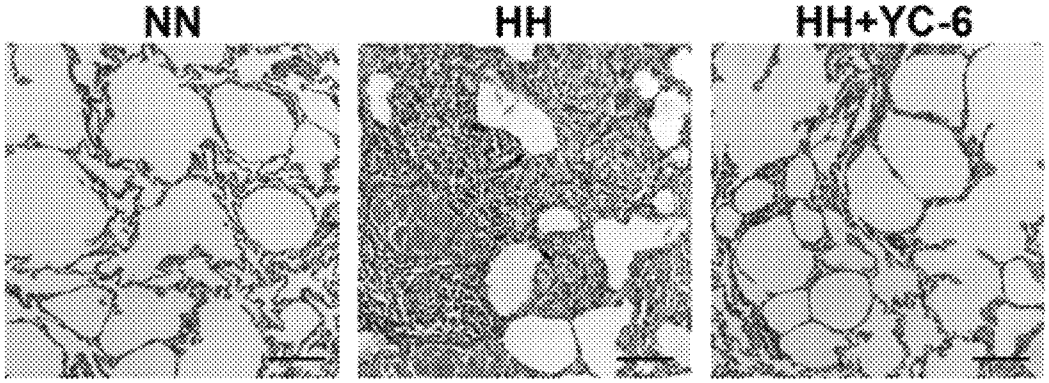
FIG. 11. YC-6 inhibited acute hypobaric hypoxia-induced inflammatory infiltration in *Macaca fasciculari* lung tissue. NN (Normobaric normoxia): normobaric normoxia group; HH (Hypobaric hypoxia): acute hypobaric hypoxia group; HH+YC-6: YC-6 treatment group. Black arrows indicate inflammatory cell infiltration in the alveolar interstitium, red arrows indicate inflammatory cell infiltration in the alveolar space, and blue arrows indicate exfoliated lung epithelial cells. The black bar represents 100 μm.

Effect of YC-6 on Lung Epithelial Cell Injury and Inflammatory Cell Infiltration In ALI/ARDS, in addition to primary disease, inflammatory cell infiltration and alveolar epithelial damage are important pathological factors. Diffuse damage and increased permeability of alveolar capillary walls, and pulmonary edema and fibrin exudation occur. Type II alveolar epithelial cell injury, reduction or disappearance of alveolar surfactant, resulted in the formation of hyaline membrane and lung collapse. All the above changes can cause oxygen diffusion disorder in the alveoli, imbalance of ventilation/perfusion ratio, hypoxemia and respiratory distress. As shown in FIG. 11, compared with the normal group, acute hypobaric hypoxia caused infiltration of inflammatory cells in the lung tissue, and a large number of inflammatory cells were observed in the alveolar membrane interstitium (black arrows) and alveolar space (red arrows). Part of the alveolar space showed shedding of damaged lung epithelial cells (blue arrows), while no obvious inflammatory infiltration and shedding of damaged lung epithelial cells were observed in the YC-6 treatment group. The above results show that YC-6 reduces vascular permeability and can effectively reduce the inflammatory infiltration of lung tissue and lung epithelial cell injury.

Experimental Results

Using the *Macaca fascicularis* lung injury model caused by acute hypobaric hypoxia in vivo, it was found by pathological detection that YC-6 significantly inhibited pulmonary vascular congestion and swelling and alveolar septum thickening, and alleviated the damage to the pulmonary air-blood barrier. YC-6 showed significant lung protection efficacy.

Example 7. YC-6 Reduced Vascular Endothelial Cell Injury Caused by Hypoxia-Related Stimulation by Promoting the Protein Expression of NR4A3

Nuclear Receptor Subfamily 4 Group A Member 3 (NR4A3), is also known as Neuron-derived Orphan Receptor-1 (NOR1). As a transcription factor, NR4A3 is involved in the regulation of physiological and pathological processes such as metabolism, inflammation, cell proliferation, apoptosis and differentiation. Knockdown of NR4A3 significantly inhibited the capillary transformation ability of vascular endothelial cells, indicating that NR4A3 has an important physiological function in vascular endothelial cells. Previous studies have shown that upregulation of NR4A3 can promote cell survival under different pathological injuries. For example, increased NR4A3 expression in vascular endothelial cells can inhibit apoptosis by upregulating cellular inhibitor of apoptosis 2 (cIAP2), thereby enhancing vascular endothelial cell survival under hypoxic conditions; in neurons increased expression of NR4A3 reduces neuronal damage caused by oxidative stress and glutamate-induced excitotoxicity.

This experiment explores whether YC-6 has a protective effect on vascular endothelial cell injury caused by hypoxia-related stimulation, and whether the related protective effect is related to the regulation of NR4A3 expression.

Experimental Materials

Cell Line

Human umbilical vein endothelial cells (HUVEC) were purchased from Guangzhou Saiku Biotechnology Co., Ltd. and cultured in modified DMEM medium (CellCook, CM2007) containing 10% fetal bovine serum. Rat vascular endothelial cells (RAOEC) were purchased from Guangzhou Genio Biotechnology Co., Ltd. and cultured in DMEM medium (Coring, 10-013-CV) containing 10% fetal bovine serum.

Tissue Sectioning

Paraffin sections of *Macaca fascicularis* lung tissue, include 3 in the normal control group (normobaric normoxia, NN), 5 in the acute hypobaric hypoxia treatment group (hypobaric hypoxia, HH), and 5 in the acute hypobaric hypoxia+YC-6 treatment group (HH+YC-6).

Main Reagents and Drugs

High glucose DMEM medium (coming, 10-03-CV)
Modified DMEM medium (CellCook, CM2007)
Australian Fetal Bovine Serum (Gibed, 10099141)
0.25% trypsin (Gibco, 25200072)
Sugar-free DMEM medium (Gibco, A1443001)
LDH Detection Kit (Promega, GI780)
20% hydroxypropyl-cyclodextrin solution (Hydroxypropyl-β-Cyclodextrin. HP-β-CD) (Guangzhou Cellprotek Pharmaceutical Co., Ltd., ampoule bottle, batch number 180502, size 5 mL: 1 g, concentration 0.2 g/ml.)
YC-6 injection ((inane/bon Cellprotek Pharmaceutical Co., Ltd., ampoule bottle, batch number 20010201, site 5 ml.: 50 mg, concentration 10 mg/ml., dissolved in 20% hydroxypropyl-cyclodextrin solution)
Cycloheximide (MCE, HY-12320)
Chloroquine (MCE, HY-17589)
MG132 (Selleck, S2619)
NAC (Selleck, S1623)
PBS (Gibco, C10010500BT)
Protease inhibitor (Targetmol, C0001)
Phosphatase inhibitor (Targetmol, 0004)
Cell lysate (Thermofisher Scientific. 78501)

BCA protein quantification kit (Thermofisher Scientific, 23225)
5× protein loading buffer (Beyotime, P0015L)
SDS-PAGE separating gel huller (Bio-rad, 161-0798)
SDS-PAGE concentrated gel buffer (Bio-rad, 161-0799)
10% SDS solution (Bio-rad, 161-0416)
30% Ace-Bis acrylamide (MIK, DB240)
Ammonium persulfate (MPbio, 1938513)
TEMED (Macklin, T6023-100 mL)
PVDF membrane (Roche, 3010040001)
Skimmed milk powder (Wako, 190-12865)
TBS (Boster, AR0031)
Anti-NR4A3 antibody (Santa cruz, sc-393902)
Anti-actin antibody (Arigo, arg62346)
Anti-CD31 antibody (Abeam, ab28364)
Goat anti-mouse IgG antibody (HRP) secondary antibody (Arigo, arg65350)
Donkey anti-Mouse IgG (H+L) Highly Cross-Adsorbed Secondary Antibody, Alexa Fluor 488 fluorescent secondary antibody (Invitrogen, A-21202)
Donkey anti-Rabbit IgG (H+L) highly Cross-Adsorbed Secondary Antibody, Alexa Fluor 555 fluorescent secondary antibody (Invitrogen Mogen, A-31572)
Hoechst33342 (Signal-Aldrich. 14533, used at 5 μg/mL)
Water-soluble covering medium (Boster, AR1018)
Chemiluminescent liquid (Merck Millipore, WBKLS0500)
10×EDTA antigen retrieval solution Mosier, AR0023)
DAKO antibody diluent (Dako. S-3022)
Xylene (Guangzhou Chemical Reagent Factory, 33535)
Anhydrous ethanol (Guangzhou Chemical Reagent Factory, 32061)
Mayer's hematoxylin staining solution (MIK, BL003)
Eosin Y (Weijia technology, 17372-87-1).
Trizol (Invitrogen, 15596)
Reverse transcriptase (Thermofisher Scientific, EP0442)
dNTPs (Sigma-Aldrich, D7295)
SuperReal PreMix SYBR Green qPCR Kit (Tiangen, FP205)
IP lysis buffer (Beyotime, P0013)
IP magnetic beads (Bimake, 1323202)

Main Experimental Equipment

Ultra-clean workbench, cell incubator, hypoxia workstation, microplate reader, chemiluminescence imager, laser confocal microscope, low temperature high-speed centrifuge, real-time fluorescence quantitative PCR system

Experimental Method

Cell Culturing, OGD-R Injury Model and Drug Treatment

HUVEC cells were cultured in modified DMEM medium containing 10% fetal bovine serum. When the cells reached about 80% confluence, the cells were digested with 0.25% trypsin, and then pipetted evenly with modified DMEM containing 10% peptide bovine serum. The cell concentration was adjusted to $1\times10^5$ cells/mL, and the cells were seeded at 400 uL/well in a 24-well plate, and the experiment was carried out when the cells grew to about 70% confluence. RAOEC cells were cultured in high-glucose DMEM medium containing 10% fetal bovine serum, and the seeding conditions were the same as those of HUVEC. During the OGD-R injury treatment, the hypoxia workstation was set to have an oxygen concentration of 1% (1% $O_2$, 5% $CO_2$, 94% $N_2$), a temperature of 37° C., and a humidity of 85%. A sugar-free DMEM medium was placed in the hypoxia workstation for pre-hypoxia for 3 hours. The medium in the culture plate was aspirated, and the plate was washed twice with preheated sugar-free DMEM medium, and 100 uL of sugar-free DMEM medium was added to each well. The culture plate was placed in the hypoxia workstation, and 300 uL of pre-hypoxic sugar-free DMEM medium was added to each well, and then the culture plate was placed in the hypoxia workstation for additional hypoxia for 4 hours. Restoration was then performed. The culture plate was taken out, and the sugar-free DMEM medium was replaced with 400 uL of normal medium containing 10% fetal bovine serum, and then the plate was placed in a 37° C. 5% $CO_2$ cell incubator for culturing for 24 hours or a specified time period. For the cells in the normal group, it was only replaced with 400 uL of new normal medium containing 10% fetal bovine serum. For the cells in the drug treatment group, after the cells were subjected to OGD treatment, and at the same time of restoration, they were given the drug at the indicated final concentration (the final concentration of YC-6 was 1 μM, 3 μM or 10 μM, and the vehicle control was given with the corresponding 20% hydroxypropyl cyclodextrin, the final concentration of cycloheximide (CHX) was 100 μM, the final concentration of chloroquine (CQ) was 10 μM, 30 μM or 100 μM, and the final concentration of MG132 was 10 nM, 30 nM or 100 nM) until the end of the experiment. The model control group was not treated with any drug.

Western Blot

The cells were washed twice with pre-cooled PBS, then scraped off with a cell scraper and transferred to a 1.5 mL centrifuge tube, and centrifugation was performed at 4° C. and 1000 g for 5 minutes. The supernatant was discarded, and an appropriate amount of cell lysate containing protease inhibitors and phosphatase inhibitors was added to the cell pellet. The cells were fully resuspended and placed on ice for 5 minutes to fully lyse the cells. Then centrifugation was performed at 12,000 g for 10 minutes at 4° C., and then the supernatant was separated, which was the extracted cellular protein. Each protein sample was then quantified using the BCA protein quantification kit. After protein quantification, protein lysis buffer was used to adjust the protein concentration of each sample to be consistent with the protein sample with the lowest concentration, and then each protein sample was sufficiently mixed with 5× protein loading buffer at a ratio of 4:1. The mixture was boiled in a boiling bath for 5 minutes, then a turbulent flow was introduced to provide an even mixing. After a short centrifugation, samples at the bottom of the tube were collected and stored on ice for later use or frozen at −80° C. The protein samples were subjected to 10% SDS-PAGE electrophoresis, and the separated proteins were then transferred to a PVDF membrane. The PVDF membrane was blocked with 5% nonfat milk for 2 hours at room temperature. After blocking, the membrane was washed for 3 times with TBST (i.e., TBS containing 1% Tween 20) for 5 minutes each time. Then, corresponding antibody was diluted with 5% BSA, and the PVDF membrane was placed in the corresponding diluted antibody, and incubation was performed at 4° C. overnight. After the incubation, the membrane was washed three times with TBST for 5 min each time. The corresponding secondary antibody was diluted with 5% BSA, and the PVDF membrane was placed in the corresponding diluted secondary antibody, and incubation was performed at room temperature for 1 hour. After the incubation, the membrane was washed three times with TBST for 5 minutes each time, and the PVDF membrane was placed in chemiluminescence solution for imaging with a chemiluminescence imager.

Tissue Immunofluorescence

The paraffin sections were placed in a 65° C. oven for 30 minutes, and then quickly transferred to 100% xylene for dewaxing, and then subjected to rehydration according to the regular process (100% xylene, 5 min—100% xylene, 2 min—100% xylene, 2 min—100% ethanol, 1 min—100% ethanol, 1 min—95% ethanol, 1 min—90% ethanol, 1 min—B0% ethanol, 1 min—70% ethanol, 1 min—50% ethanol, 1 min—distilled water, 1 min×3), and then EDTA antigen retrieval solution (microwave heating) was used for antigen retrieval. After the retrieval, it was naturally cooled to room temperature, and then washed three times with PBS for 5 minutes each time. The residual PBS on the tissue section was removed. A circle was drew around the tissue with an immunohistochemical pen, and then the corresponding primary antibody diluted in DAKO antibody diluent was added to the tissue to make it completely cover the tissue. The tissue section was incubated overnight in a humidified chamber at 4° C. Then it was washed 3 times with PBS for 5 minutes each time. Then the corresponding diluted fluorescent secondary antibody was added to the tissue, and incubation was performed in a humid chamber for 1 hour at room temperature in the dark. Then it was washed 3 times with PBS for 5 minutes each time. Nuclei were stained with Hoechst 33342 and incubation was performed for 5 minutes at room temperature in a humid chamber in the dark. Then it was washed with PBS three times for 5 minutes each time, covered with water-soluble mounting medium, and then imaged with a laser confocal microscope.

Hematoxylin-Cosin (HF) Staining

Paraffin sections were rehydrated as previously described. The sections were then immersed in hematoxylin staining solution and stained at room temperature for 10 minutes. The sections were gently rinsed with running water to remove excess hematoxylin, and then differentiated with 1% hydrochloric acid-ethanol for 10 seconds. The sections were then gently rinsed with running water for 5 minutes, then returned to blue with 1% ammonia for 10 seconds or under running water for 30 minutes. The sections were gently rinsed with running water for 5 minutes, then immersed in 1% eosin, and stained at room temperature for 5 minutes. The sections were gently rinsed with running water to remove excess eosin staining solution. The sections were successively immersed in 70% ethanol (1 min)-80% ethanol (1 min)-90% ethanol (1 min)-95% ethanol (1 min)-100% ethanol (1 min)-100% ethanol (1 min)-xylene (5 min)-xylene (5 min) for dehydration for transparency, and then covered with neutral resin (diluted with appropriate amount of xylene, about 50% xylene). The sections were placed in a fume hood, and after the covering medium was dried out, a Nikon Eclipse Ti-U inverted fluorescence microscope was used for bright field photography, and each individual was photographed in a random field of view for subsequent pathological analysis.

Cell Immunofluorescence Staining

At the end of the experiment, the cells were quickly washed twice with PBS, then 4% paraformaldehyde was added, and the cells were placed at room temperature for 15 minutes. The membranes were then incubated with PBS containing 0.2% TritonX-100 for 15 minutes at room temperature. The cells were washed three times with PBS, then the corresponding primary antibodies diluted in DAKO antibody diluent were added and incubation was performed overnight at 4° C. The primary antibody was removed by aspiration, and the cells was washed three times with PBS, then the diluted fluorescent secondary antibody was added, and incubation was performed at room temperature for 1 hour in the dark. The secondary antibody was removed by aspiration, and the cells was washed three times with PBS, then hoechst33342 was added to stain the nuclei, and incubation was performed at room temperature for 5 minutes in the dark Hoechst33342 was removed by aspiration, the cells were washed three times with PBS, 200 uL of PBS was added, and images were taken with a confocal microscope.

Real-Time Fluorescent Quantitative PCR

At the end of the experiment, the cell culture medium was discarded, and then an appropriate amount of Trizol reagent was directly added. After fully lysing the cells on ice, the Trizol lysate was transferred to a 1.5 ml, centrifuge tube with no RNase, and then chloroform was added in an amount of 20% of that of Trizol. The tube was shaken vigorously for 15 seconds, and placed on ice for 10 minutes. Centrifugation was performed at 12,000 g for 15 minutes at 4° C., then the upper liquid was transferred to a new 1.5 mL centrifuge tube (the middle and lower layers were not touched). Isopropanol was added in a volume of 0.8 times the volume of the upper liquid, and the tube was turned upside down several times for an even mixing, and placed on ice for 10 minutes. Then centrifugation was performed at 12,000 g at 4° C. for 15 minutes, the isopropanol was carefully discarded, 1 mL of pre-cooled 75% ethanol (absolute ethanol was diluted to 75% with DEPC water) was added to the bottom of the tube, and the centrifuge tube was turned upside down to allow the the sediment at the bottom of the tube float up. Then centrifugation was performed at 12,000 g for 15 minutes at 4° C., the 75% ethanol was discarded, and new pre-cooled 75% ethanol was used for washing again. Centrifugation was performed at 12,000 g for 15 minutes at 4° C., the 75% ethanol was discarded, and then a short centrifugation was performed again and the remaining ethanol was removed with a pipette. The centrifuge tube was placed on the ultra-clean workbench and the tube was left open for 5 to 10 minutes to allow the ethanol to evaporate. An appropriate amount of DEPC water was added to dissolve RNA, and Nanodrop ultra-trace UV spectrophotometer was used to measure the OD value for quantification. OD260/280 in the range of 1.8-2.0 indicated that the quality of RNA was high. RNA was reversely transcribed and real-time fluorescent quantitative PCR was performed as follows:

1) Pre-denaturation: Total RNA 2 μg, Oligo dT 1 μL, DEPC·$H_2O$ to 13 μL, well mixed, 65° C., 5 min, put on ice immediately after completion
2) Reverse transcription: 5× Reaction Buffer 4 μL, dNTP mix 2 μL, Reverse Transcriptase 1 μL, well mixed, 42° C. 60 min, 70° C. 10 min, 4° C. forever
3) Real-time PCR (ABI 7500 fast real-time PCR system)

Primer stock solution: 100 nmol/μL (primer lyophilized powder+nmoles*10 μL RNase-free dd$H_2O$), primer working solution 2 nmol/μL (4 μL, FP+4 μL RP+192 μL RNase-free dd$H_2O$) and SYBR Green Mix/ROX=1.25 mL/50 μL, the following solutions were well mixed SYBR Green/ROX 5 μL, cDNA 1 μL, Primer 2 μL, DEPC·H2O 2 μL and well mixed; PCR reaction was carried out, cycle parameters Holding stage: 95° C., 15 min; Cycling stage (40 cycles): 95V, 10 s→56° C., 20 s→72° C., 30 s; Melt Curve stage (continuous): 95° C., 15 s→65° C., 60 s→>95° C., 15 s→65° C., 15 s; The relative expression was calculated using Comparative ΔΔCt method ($RQ=2^{-\Delta\Delta Ct}$) for data analysis. Primer sequences included: β-actin (human) forward: 5'-GATTCCTATGTGGGCGACGA-3'; reverse: 5'-AGGTCTCAAACATGATCTGGGT-3';NR4A3 (human) forward: 5'-AGCGGCGGCATCCTC-3'; reverse: 5'-CTAAGGGTCCAGGCTCAGG-3'; β-actin (rat) forward: 5'-CGCGAGTACAACCTTCTTGC-3'; reverse: 5'-CGT- CATCCATGGCGAACTGG-3';NR4A3 (rat) forward: T-GGAAACGTGGCGACATCCT-3'; reverse: 5'-CAGTGGGCTTTGGGTTCTGTG-3'.

Immunoprecipitation

The cells were washed twice with pre-cooled PBS, then scraped off with a cell scraper and transferred to a 1.5 mL centrifuge tube, and centrifugation was performed at 4° C. and 1000 g for 5 minutes. The supernatant was discarded, and an appropriate amount of IP lysate containing protease inhibitors and phosphatase inhibitors was added to the cell pellet. The cells were fully resuspended and placed on ice for 5 minutes to fully lyse the cells. Then centrifugation was performed at 12,000 g for 10 minutes at 4° C., and then the supernatant was separated, which was the extracted cellular protein. Each protein sample was then quantified using the BCA protein quantification kit. After protein quantification, IP lysis buffer was used to adjust the protein concentration of each sample to 1 mg/mL. An equal volume of each sample was taken to a new centrifuge tube (the remaining amount of each sample was used as input), and the corresponding amount of antibody was added according to the antibody instructions. The tube was slowly turned upside down to provide an even mixing at 4° C. overnight. Then, the IP magnetic beads were washed twice with IP lysis solution, an equal amount of IP magnetic beads were added to each sample, and the tube was continuously slowly turned upside down to provide an even mixing at 4° C. for 2 hours. The magnetic beads were then separated, and the IP magnetic beads were washed 5 times with IP lysis solution, during each time the tube was slowly turned upside down to provide an even mixing at 4° C. for 5 minutes. After the magnetic beads were separated for the last time, an equal amount of 1× protein loading buffer (IP lysis buffer and 5× protein loading buffer were mixed at a ratio of 4:1) was added to each sample. After a short centrifugation, the tube was boiled in a boiling bath for 5 minutes, then a short centrifugation was performed and the sample at the bottom of the tube was collected, the boiled sample was transferred to a new centrifuge tube, the magnetic beads were discarded, and the sample can be stored on ice for later use or frozen at −80° C. The protein sample was subjected to 10% SOS-PAGE electrophoresis, and the subsequent operations were the same as those of western blotting.

Statistics

Statistical results were presented as mean±standard deviation. One-way analysis of variance (ONE-WAY ANOVA) was used for statistical analysis, and Tukey's method was used for multiple comparisons, and $P<0.05$ was considered to be statistically significant.

Experimental Results

Figure 12:
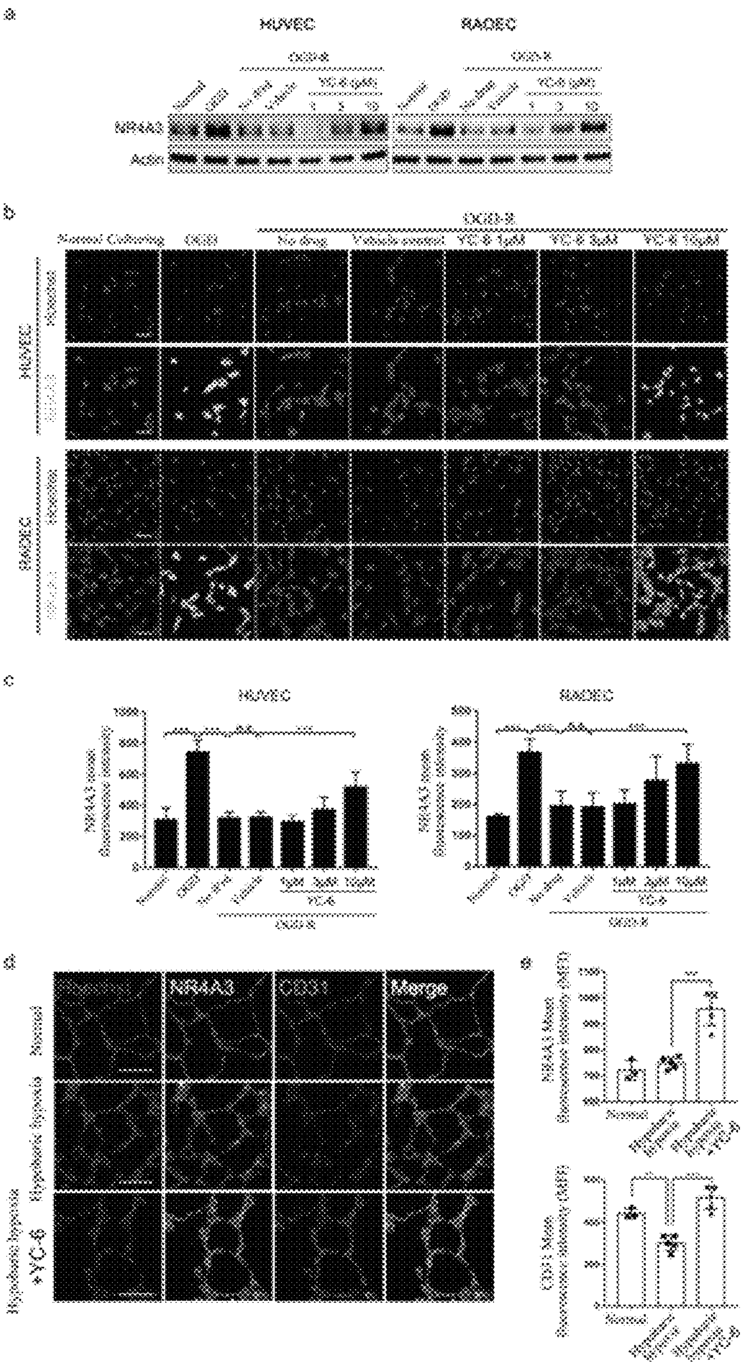
FIG. 12. YC-6 up-regulated the expression of NR4A3 protein in vascular endothelial cells and reduced cell damage under the stimulation of OGD-R/hypoxia. (a) Western blot to detect NR4A3 protein expression levels in HUVEC and RAOEC cells in normal culturing, OGD, and OGD-R. The vehicle or YC-6 was administered simultaneously with the restoration treatment. (b) Representative images of NR4A3 immunofluorescence staining of HUVEC and RAOEC cells under the same treatment in panel (a). Scale bar indicates 50 μm. (c) Quantification of the mean fluorescence intensity of NR4A3 processed in panel (b). (d) Representative images of NR4A3/CD31 fluorescent double-staining of non-human primate *Macaca fasciculari* lung tissue under normal environment (normobaric and normoxic), hypobaric hypoxia, and hypobaric hypoxia+YC-6 conditions. The white scale indicates 100 μm. (e) Quantification of the mean fluorescence intensity of NR4A3 co-localized with CD31 signal and the mean fluorescence intensity of CD31 processed for panel (d). The number of samples for normal, hypobaric hypoxia and hypobaric hypoxia+YC-6 treatment was 3, 5 and 5, respectively. Statistical methods for panels (c) and (e) were performed by one-way ANOVA for statistical analysis, and Tukey's method was used for multiple comparisons; n.s. means no statistical difference;  means P less than 0.01; * means P less than 0.001.

YC-6 Increased the Expression of NR4A3 Protein in Vascular Endothelial Cells and Reduced Cell Damage Under OGD-R/Hypoxia Stimulation It has been reported that vascular endothelial cells can reduce apoptosis by up-regulating NR4A3 and promoting the expression of downstream cIAP2 under hypoxia stimulation, indicating that the expression of NR4A3 under hypoxia-related stimulation plays an important role in promoting the survival of vascular endothelial cells. Our results showed that OGD treatment for 4 hours caused an increase in the protein expression of NR4A3 in HUVECs and RAOECs, but restoration for 24 hours caused a down-regulation of NR4A3 protein levels (FIG. 12*a*) and increased cellular LDH release (FIG. 3), suggesting that OGD-R may promote cell damage by downregulating the expression of NR4A3. Restoration injury and administration of YC-6 at the same time can dose-dependently increase the protein expression of NR4A3 (FIG. 12*a*), while dose-dependently reduce the cell damage caused by OGD-R (FIG. 3), indicating that YC-6 can play a role in protecting vascular endothelial cells by up-regulating the expression of NR4A3. The expression of NR4A3 was analyzed by cell immunofluorescence method. Consistent with the results of western blot, restoration injury and simultaneous administration of YC-6 could increase the protein expression of NR4A3 in a dose-dependent manner (FIG. 12*b-c*).

We further investigated the effect of YC-6 on the expression of NR4A3 in a pathological model of acute hypobaric hypoxia-induced lung injury in *Macaca fascicularis*. The results showed that YC-6 significantly increased the protein expression of NR4A3 in *Macaca fascicularis* lung tissue endothelial cells under the stimulation of acute hypobaric hypoxia, and inhibited the down-regulation of the expression of vascular endothelial cell marker CD31 caused by acute hypobaric hypoxia (FIG. 12*d-e*). However, the previous histopathological results (FIG. 8-FIG. 11) showed that the alveolar structure of the *Macaca fascicularis* lung tissue in the normal control group was polygonal or circular thin-walled vacuoles with clear boundaries, and the alveolar septum was a thin-walled structure and capillaries cross-sections could be seen in the septum. Acute hypobaric hypoxia caused severe tissue loosening, vascular congestion, alveolar wall thickening, exudation of red blood cells in the alveolar space, formation of hyaline membranes, and infiltration of alveoli by inflammatory cells. The formation of hyaline membranes is considered a typical case feature of diffuse alveolar injury, suggesting that acute hypobaric hypoxia causes diffuse alveolar injury and increased permeability of the lung endothelial barrier. Administration of YC-6 improved the pathological changes of lung tissue caused by acute hypobaric hypoxia and reduced the increase of gas-blood barrier permeability. Our results show the importance of NR4A3 in reducing vascular endothelial cell injury induced by hypoxia-related stimulation, and YC-6 can up-regulate NR4A3 protein expression and attenuate vascular endothelial cell injury induced by OGD-R and damage to the endothelial barrie induced by acute hypobaric hypoxia.

YC-6 Inhibited the Ubiquitination Degradation of NR4A3 Induced by OGD-R

Figure 13:
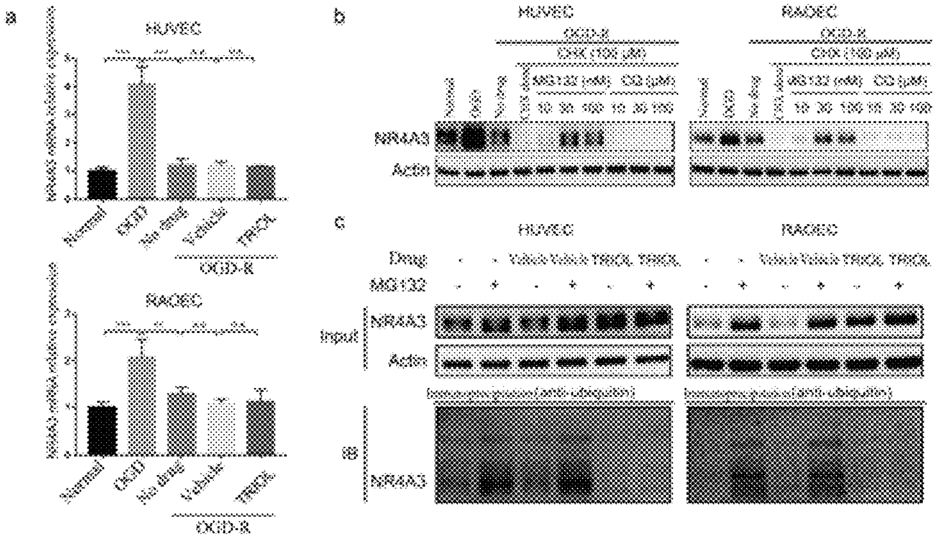
FIG. 13. YC-6 inhibited the ubiquitination and degradation of NR4A3 in vascular endothelial cells induced by OGD-R. (a) Real-time fluorescent quantitative PCR to detect the relative expression levels of NR4A3 mRNA in HUVEC and RAOEC cells under normal culturing, OGD, OGD-R, and OGD-R+YC-6. Vehicle or 10 μM YC-6 was administered to cells concurrently with the restoration treatment. (b) Western blot to detect of NR4A3 protein expression in HUVEC and RAOEC cells under normal culturing, OGD, OGD-R, and OGD-R+different drug treatments. Cycloheximide (CHX), MG132 and chloroquine (CQ) were administered during restoration. (c) Immunoprecipitation experiments with anti-ubiquitin antibodies to detect changes in NR4A3 ubiquitination modification after OGD-R and OGD-R+drug treatment YC-6 was used at a concentration of 10 μM, and MG132 was used at a concentration of 100 nM. (a) For the statistical method of the relative expression level of NR4A3 mRNA in the figure, one-way ANOVA was used for statistical analysis, and Tukey's method was used for multiple comparisons, n.s. indicates no statistical difference;  means P less than 0.01; * means P less than 0.001. CHX means cycloheximide and CQ means chloroquine. Input represents the initial sample used for immunoprecipitation, and IB represents immunoblot detection.

Previous studies have shown that the protein expression of NR4A3 is mainly regulated at the transcriptional level, and HIF-1α is an upstream transcription factor that regulates the expression of NR4A3 under hypoxia. Therefore, we investigated whether YC-6 promotes NR4A3 protein expression by promoting its transcriptional level. The results showed (FIG. 13) that OGD caused a significant increase in the transcription level of NR4A3, indicating that OGD promotes the expression of NR4A3 by stimulating the transcription of HIF-1α, which may be a self-protection of vascular endothelial cells against hypoxia-related injury mechanism. Restoration caused a decrease in the transcription level of NR4A3, but YC-6 did not significantly up-regulate the transcription level of NR4A3, indicating that YC-6 did not increase NR4A3 protein expression by promoting its the transcription. Therefore, we further investigated the possibility of YC-6 inhibiting the degradation of NR4A3. HUVEC and RAOEC were subjected to OGD treatment, and cycloheximide (CHX) was given to inhibit protein synthesis during restoration. The results showed that inhibition of protein synthesis resulted in almost complete depletion of NR4A3 protein, indicating that NR4A3 protein was rapidly degraded during restoration injury. In order to further investigate the degradation pathway of NR4A3, at the same time as CHX was administered during restoration injury, different concentrations of ubiquitin proteasome inhibitor MG132 and lysosomal degradation inhibitor chloroquine CQ were administered to block the protein degradation in different ways. The results showed that under restoration injury, simultaneous administration of CHX and MG132 could inhibit the degradation of NR4A3, but administration of CHX and CQ did not significantly inhibit the degradation of NR4A3, indicating that the degradation of NR4A3 during restoration injury was mainly through the ubiquitin proteasome system.

To further explore whether YC-6 inhibited the ubiquitination degradation of NR4A3 protein under restoration conditions, we performed protein extraction to the restored cells and immunoprecipitation experiments with anti-ubiquitin antibodies. The results showed that restoration injury caused the ubiquitination modification of NR4A3. Restoration injury and administration of MG132 at the same time could lead to the increase of ubiquitinated NR4A3. The ubiquitination modification of NR4A3 was not significantly affected by solvent treatment after restoration, but administration of YC-6 could inhibit the ubiquitination of NR4A3 induced by restoration. After restoration, administration of MG132 and YC-6 did not significantly increase the ubiquitination of NR4A3, indicating that YC-6 inhibited the ubiquitination modification of NR4A3.

Our results suggest that YC-6 inhibits the degradation of NR4A3 by inhibiting its ubiquitination modification under restoration injury, thereby promoting the survival of vascular endothelial cells under injury stimulation.

In conclusion, YC-6 can reduce the damage of vascular endothelial cells caused by OGD-R. One of the mechanisms is that YC-6 inhibits the ubiquitination and degradation of NR4A3, thereby promoting the survival of vascular endothelial cells under pathological stimulation. In overall animals, YC-6 promotes the protein expression of NR4A3 in pulmonary vascular endothelial cells under hypoxia stimulation, reduces hypoxia-induced increase in lung endothelial barrier permeability and related pathological changes, and plays a role in lung protection.

REFERENCES

Du Jingxia, Wei Guohui. Changes in the structure and function of pulmonary vascular endothelial cells and acute lung injury[J]. Hebei Medical Journal. 2012, 34(23):3624-3626.

Wu Erbin, Li Lihua, Guo Zijian. Expression of PFKFB3 in liver cancer and its clinical significance[J]. Chinese Clinical Oncology, 2014(6):508-511.

Song Xuhua. Expression of TUM2-PK, PFKFB3 and TKTL1 in laryngeal carcinoma and its clinical significance[D].

Zhang Mimi, He Yuejun. Expression of PFKFB3 in patients with colon cancer and its clinical significance[J]. Chinese Journal of Clinical Medicine, 2017, 024(004):587-590.

Wei Lai. Expression of 6-phosphofructo-2-kinase in colorectal cancer, and its clinical significance and function [D]. 2017, Cui Zhang Yanhong, Yin Xiuyan, et al. Discussion on the mechanism of the effect of PFKFB3 on cervical cancer cells[J]. Chinese Journal of Cancer Prevention and Treatment, 2018, 25(24):7-13.

Xue Xiaoying. Study on the mechanism in targeting PFKFB3 to regulate the differentiation of CD4~+ T cells to alleviate experimental autoimmune encephalomyelitis [D]. 2018.

Chen Xiangrong, Du Jumei, Wu Zongtao. Expression of PFKFB3 in glioma tissue and its effect on the malignant biological behavior of H4 cells[J]. Chinese Journal of Cancer Biotherapy. 2018, 025(004):363-369.

Chen Yongcheng, Luo Zhizhai, Lu Guanming. Expression of PFKFB3 in papillary thyroid carcinoma and its significance[J]. Chinese Journal of Cancer Prevention and Treatment, 2018, 025(004):250-257.

Hu Zhihui, Duan Yanan, Han Lujun. PFKFB3 gene enhances the effect of apatinib on apoptosis in gastric cancer and its mechanism[J]. Chinese Journal of Integrated Traditional and Western Medicine on Digestion, 2019.

Wang Chunhui. Study of the effect of PFKFB3 antagonist PFK15 in inhibiting autophagy and proliferation of rhabdomyosarcoma cells[D]. 2018.

Zhao Jiajia, Tang Qingming. Yu Ran, et al. Regulation mechanism of effective inhibition of tongue cancer progression by biorhythmicity of PFKFB3[C]/Collection of papers in the 6th Academic Conference of the General Stomatology Professional Committee of the Chinese Stomatological Association and the 2015 Annual Conference of the General Stomatology Professional Committee of the Guangdong Stomatological Association. 2015.

Li Jijia, Wang Weiming. PFKFB3 mediates CD163+ tumor-associated macrophage infiltration to regulate oral cancer angiogenesis[C]/Collection of papers in the 9th General Stomatology Academic Conference of Chinese Stomatological Association. 2018.

Wu Hui. Study on the effect and mechanism of glycolysis on PD-L1/PD-1 molecule expression in bladder tumors[D]. 2019.

Qin Pengjun. Study on the mechanism of sunitinib inducing autophagy in renal cancer cells[D]. 2015.

Hon Yunlei, Zhang Yu, Xia Juanjuan, et al. Research progress of 6-phosphofructo-2-kinase 3 inhibitors[J]. Chinese Journal of Medicinal Chemistry, 2016(1):65-70.

Atsumi T, Chesney J, Metz, C, et al. High expression of inducible 6-phosphofructo-2-kinase/fructose-2,6-bisphosphatase (iPFK-2: PFKFB3) in human cancers[J]J. Cancer Res. 2002, 62(20):5881-7.

Yang J G, Wang W M, Xia H F, et al. Lymphotoxin-α promotes tumor angiogenesis in HNSCC by modulating glycolysis in a PFKFB3-dependent manner[J]. Int J Cancer. 2019, 145(5):1358-1370.

Zheng W D. Zhou F L, Lin N MicroRNA-26b inhibits osteosarcoma cell migration and invasion by down-regulating PFKFB3 expression[J]. Genetics and Molecular Research, 2015, 14(4):16872-16879.

Zhu Y, Lu L, Qiao C, et al. Targeting PFKFB3 sensitizes chronic myelogenous leukemia cells to tyrosine kinase inhibitor[J]. Oncogene, 2018.

Hu X, Xu Q, Wan H, et al. PI3K-Akt-mTOR/PFKFB3 pathway mediated lung fibroblast aerobic glycolysis and collagen synthesis in lipopolysaccharide-induced pulmonary fibrosis[J]. Lab Invest. 2020.

Lypova N, Telang S, Chesney J, et al. Increased 6-phosphofructo-2-kinase/fructose-2,6-bisphosphatase-3 activity in response to EGFR signaling contributes to non-small cell lung cancer cell survival[J]. Journal of Biological Chemistry, 2019, 294.

Laszlo Kovacs, Yapeng Cao, Weihong, et al. HanPFKFB3 in Smooth Muscle Promotes Vascular Remodeling in Pulmonary Arterial Hypertension[J]. American journal of respiratory and critical care medicine. 2019.
Lina Wang, Yapeng Cao, B. Gorshkov, et al. Ablation of endothelial Pfkfb3 protects mice from acute lung injury in LPS-induced endotoxemia[J]. Pharmacological Research. 2019.
Li X, Liu J, Qian L, et al. Expression of PFKFB3 and Ki67 in lung adenocarcinomas and targeting PFKFB3 as a therapeutic strategy. Mol Cell Biochem. 2018, 445(1-2): 123-134.
CLME B, TELANG S, CLEM A, et al. Small-molecule inhibition of 6-phosphofructo-2-kinase activity suppresses glycolytic flux and tumor growth[J]. Mol Cancer Ther, 2008, 7(1): 110-120.
BANDO H, ATSUMI T, NISHIO T, et al. Phosphorylation of the 6-phosphofructo-2-kinase/fructose 2,6-bisphosphatase/PFKFB3 family of glycolytic regulators in human cancer[J]. Clin Cancer Res. 2005, 11(16):5784-5792.
Butt Y, Kurdowska A, Allen T C. Acute Lung Injury: A Clinical and Molecular Review. Arch Pathol Lab Med. 2016; 140(4): 345-50.
Clem B, et al. Small-molecule inhibition of 6-phosphofructo-2-kinase activity suppresses glycolytic flux and tumor growth. Mol Cancer Ther. 2008 January; 7(1):110-20.
Gong Y, Lan H, Yu Z, Wang M, Wang S, Chen Y, Rao H, Li J, Sheng Z, Shao J, Blockage of glycolysis by targeting PFKFB3 alleviates sepsis-related acute lung injury via suppressing inflammation and apoptosis of alveolar epithelial cells. Biochem Biophys Res Commun. 2017 Sep. 16; 491(2):522-529.
Cao Y, Zhang X, Wang L, Yang Q, Ma Q, Xu J, Wang J, Kovacs L, Ayon R J, Liu Z, Zhang M, Thou Y, Zeng X, Xu Y, Wang Y, Fulton D J, Weintraub N L, Lucas R, Dong Z, Yuan J X, Sullivan J C. Meadows L. Barman S A. Wu C. Quan J, Hong M, Su Y, Huo Y.PFKFB3-mediated endothelial glycolysis promotes pulmonary hypertension. Proc Natl Acad Sci USA. 2019 Jul. 2; 116(27):13394-13403.
Kovacs L, Cao Y, Han W, Meadows L, Kovacs-Kasa A, Kondrikov D, Verin A D, Barman S A, Dong Z, Huo Y, Su Y. PFKFB3 in Smooth Muscle Promotes Vascular Remodeling in Pulmonary Arterial Hypertension. Am J Respir Crit Care Med. 2019 Sep. 1; 200(5):617-627.
Shi L, Pan H, Liu Z, Xie J, Han W, Roles of PFKFB3 in cancer, Signal Transduct Target Ther. 2017 Nov. 24; 2:17044.
Klarer A C, O'Neal J, Imbert-Fernandez Y, Clem A, Ellis S R, Clark J, Clem B, Chesney J, Telang S, Inhibition of 6-phosphofructo-2-kinase (PFKFB3) induces autophagy as a survival mechanism. Cancer Metab. 2014 Jan. 23; 2(1):2.
Teuwen L A, Draoui N, Dubois C, Carmeliet P. Endothelial cell metabolism: an update, 2017. Curr Opin Hematol. 2017 May; 24(3):240-247,
Cantelmo A R. Brajic A, Carmeliet P. Endothelial Metabolism Driving Angiogenesis: Emerging Concepts and Principles. Cancer J. 2015 July-August; 21(4):244-9.
Smith K M, Mrozek J D, Simonton S C, et al. Prolonged partial liquid ventilation using conventional and high-frequency ventilatory techniques: gas exchange and lung pathology in an animal model of respiratory distress syndrome. Crit Care Med. 1997; 25(11): 1888-97.
Wu F, Zhao S, Yu B, Chen Y-M, Wang W, Song Z-G, Hu Y, Tao Z-W, Tian J-H, Pei Y-Y et al: A new coronavirus associated with human respiratory disease in China. *Nature* 2020.
Huang C, Wang Y, Li X, Ren L, Zhao J, Hu Y, Zhang L, Fan G, Xu J, Gu X et al: Clinical features of patients infected with 2019 novel coronavirus in Wuhan. China. The Lancet 2020, 395(10223):497-506.
Xu Z, Shi L, Wang Y, Zhang J, Huang L, Zhang C, Liu S, Zhao P, Liu H, Zhu L et al: Pathological findings of COVID-19 associated with acute respiratory distress syndrome. *The Lancet Respiratory Medicine.* 2020
Gong Y, Lan H, Yu Z, Wang M, Wang S, Chen Y, Rao H, Li J, Sheng Z, Shao J: Blockage of glycolysis by targeting PFKFB3 alleviates sepsis-related acute lung injury via suppressing inflammation and apoptosis of alveolar epithelial cells. Biochem Biophys Res Commun 2017, 491 (2):522-529.
Wang L, Cao Y, Gorshkov B, Zhou V, Yang Q, Xu J, Ma Q, Zhang X, Wang J, Mao X et al: Ablation of endothelial Pfkfb3 protects mice from acute lung injury in LPS-induced endoloxemia. Pharmacol Res 2019, 146:104292.
Cao V, Zhang X, Wang L, Yang Q, Ma Q, Xu J, Wang J, Kovacs L, Ayon R J, Liu Z et al: PFKFB3-mediated endothelial glycolysis promotes pulmonary hypertension. Proc Natl Acad Sci USA 2019, 116(27):13394-13403.

The invention claimed is:

1. A method for treating a disease mediated by lung epithelial cell injury in a subject, the method comprising administering to the subject an effective amount of a compound of formula I:

(formula I)

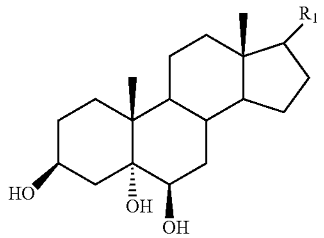

or a deuterated compound or a pharmaceutically acceptable salt thereof, wherein $R_1$ is selected from H, —CN, fluoro, chloro, $C_{1-10}$ alkyl, fluoro or chloro substituted $C_{1-10}$ alkyl, $C_{1-10}$ alkoxy, fluoro or chloro substituted $C_{1-10}$ alkoxy, and $C_{3-10}$ cycloalkyl, wherein the disease mediated by lung epithelial cell injury is selected from one or more of acute lung injury, acute respiratory distress syndrome, pulmonary fibrosis, chronic lung disease in premature infants, chronic obstructive pulmonary disease, and pneumocystis disease.

2. The method of claim 1, wherein $R_1$ is H, $—CHCH_2CH_3$, $—CH(CH_3)_2$, $—CH(CH_2)_3CH_3$, or $—CH(CH_3)(CH_2)_3CH(CH_3)_2$.

3. The method of claim 1, wherein $R_1$ is H.

4. The method of claim 1, wherein the acute lung injury or acute respiratory distress syndrome is caused by hyperoxia, viral infection, bacterial infection, trauma, shock, ischemia-reperfusion, acute pancreatitis, inhalation injury, diffuse alveolar damage, or poisoning.

5. The method of claim 4, wherein the virus is a coronavirus, influenza virus, respiratory syncytial virus, adenovirus, parainfluenza virus, measles virus, cytomegalovirus, or a combination thereof.

6. The method of claim 5, wherein the virus is a coronavirus.

7. The method of claim 6, wherein the coronavirus is SARS-CoV-2.

8. The method of claim 1, wherein the acute lung injury is a lung injury caused by a surgery.

9. The method of claim 8, wherein the surgery is pneumonectomy, lung tumor resection, or lung transplantation.

10. The method of claim 9, wherein the pneumonectomy is sublobectomy, lobectomy, or total pneumonectomy.

11. The method of claim 1, wherein the disease mediated by lung epithelial cell injury is manifested as overexpression of PFKFB3 protein.

* * * * *